United States Patent
Humayun et al.

(10) Patent No.: US 12,427,303 B2
(45) Date of Patent: Sep. 30, 2025

(54) BIOELECTRONIC LENS (E-LENS) SYSTEM FOR ELECTRICAL STIMULATION AND NEUROPROTECTION OF THE RETINA

(71) Applicant: UNIVERSITY OF SOUTHERN CALIFORNIA, Los Angeles, CA (US)

(72) Inventors: Mark S. Humayun, Glendale, CA (US); Gianluca Lazzi, Los Angeles, CA (US); Bodour Salhia, Los Angeles, CA (US); Manjunath Machnoor, Los Angeles, CA (US); Javad Paknahad, Los Angeles, CA (US); Alejandra Gonzalez-Calle, Los Angeles, CA (US); Ben Yi Tew, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/685,186

(22) Filed: Mar. 2, 2022

(65) Prior Publication Data
US 2022/0280777 A1    Sep. 8, 2022

Related U.S. Application Data

(60) Provisional application No. 63/277,980, filed on Nov. 10, 2021, provisional application No. 63/155,715, filed on Mar. 2, 2021.

(51) Int. Cl.
*A61N 1/04*    (2006.01)
*A61N 1/05*    (2006.01)
(Continued)

(52) U.S. Cl.
CPC ......... *A61N 1/0464* (2013.01); *A61N 1/0456* (2013.01); *A61N 1/0492* (2013.01);
(Continued)

(58) Field of Classification Search
CPC .. A61N 1/0464; A61N 1/0456; A61N 1/0492; A61N 1/0543; A61N 1/14; A61N 1/40; A61N 1/36046; A61N 1/36014
See application file for complete search history.

(56) References Cited

U.S. PATENT DOCUMENTS

| 7,877,148 B2 | 1/2011 | Chowdhury et al. |
| 2004/0106965 A1 * | 6/2004 | Chow .................. A61N 1/0543 607/54 |

(Continued)

FOREIGN PATENT DOCUMENTS

WO    WO-2020264263 A1 * 12/2020

OTHER PUBLICATIONS

International Search Report and Written Opinion (mailing date Jun. 15, 2022) for Corresponding International PCT Patent Application No. PCT/US2022/018542, filed Mar. 2, 2022 (7 pages).

*Primary Examiner* — Benjamin J Klein
*Assistant Examiner* — Daniel Tehrani

(57) ABSTRACT

Bioelectronic lens (E-lens) systems for inducing neuroprotective changes in neurons, in particular the retina. A system may include a stimulating electrode configured to be placed on an eye or skin around the eye. The system may further include a return electrode configured such that voltage distribution is focalized to the eye and induced electric fields to an area of interest on the eye or on the skin around the eye are maximized. The electric fields provide neuroprotection and reinnervation.

18 Claims, 44 Drawing Sheets

(51) Int. Cl.
 *A61N 1/14* (2006.01)
 *A61N 1/40* (2006.01)
(52) U.S. Cl.
 CPC ............. *A61N 1/0543* (2013.01); *A61N 1/14* (2013.01); *A61N 1/40* (2013.01)

(56) References Cited

U.S. PATENT DOCUMENTS

| | | |
|---|---|---|
| 2005/0010266 A1 | 1/2005 | Bogdanowicz |
| 2006/0142857 A1 | 6/2006 | Chow et al. |
| 2009/0287275 A1 | 11/2009 | Suaning et al. |
| 2012/0130398 A1 | 5/2012 | Ackermann et al. |
| 2016/0016014 A1* | 1/2016 | Wagner .................. A61N 7/00 601/2 |
| 2018/0078767 A1* | 3/2018 | Rapoport ............. A61N 1/0534 |
| 2018/0104475 A1* | 4/2018 | Ho ....................... A61N 1/3787 |
| 2019/0344076 A1* | 11/2019 | Irazoqui .................. G02C 7/04 |
| 2020/0101290 A1* | 4/2020 | Rockley ............ A61N 1/36046 |
| 2020/0171307 A1* | 6/2020 | Rockley ............ A61N 1/36046 |
| 2021/0022948 A1* | 1/2021 | Musallam ............... A61K 35/19 |
| 2021/0085977 A1* | 3/2021 | Chew .................... A61N 1/205 |

* cited by examiner

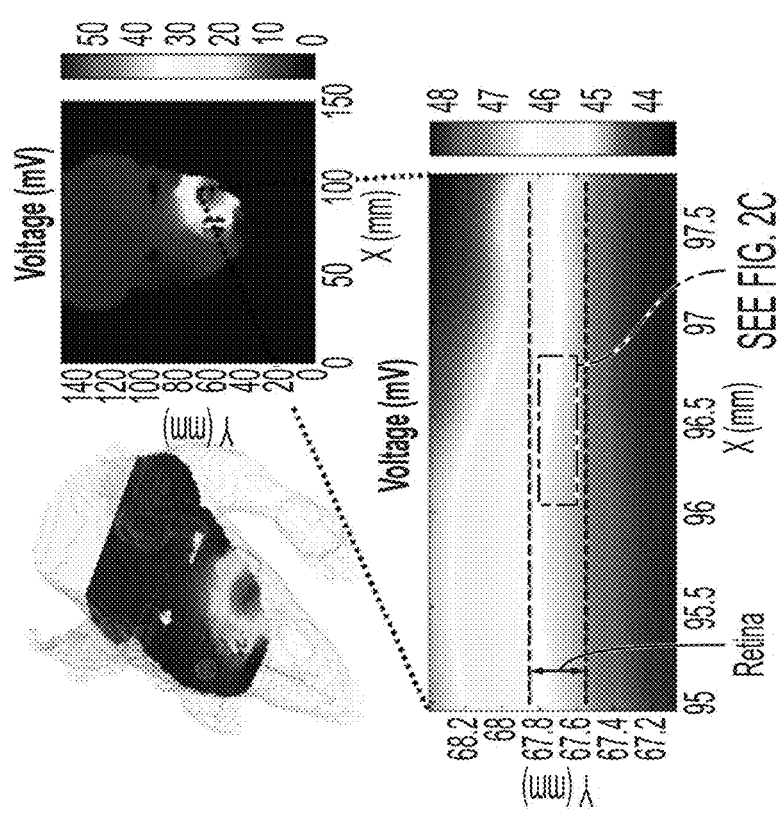
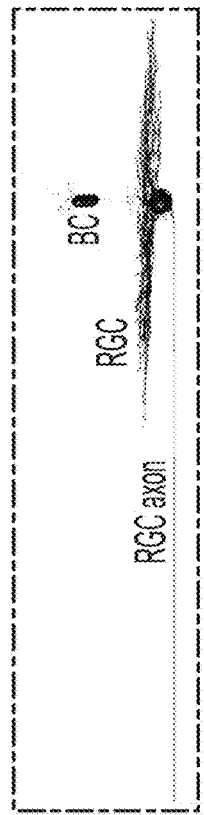
FIG. 2B
FIG. 2C
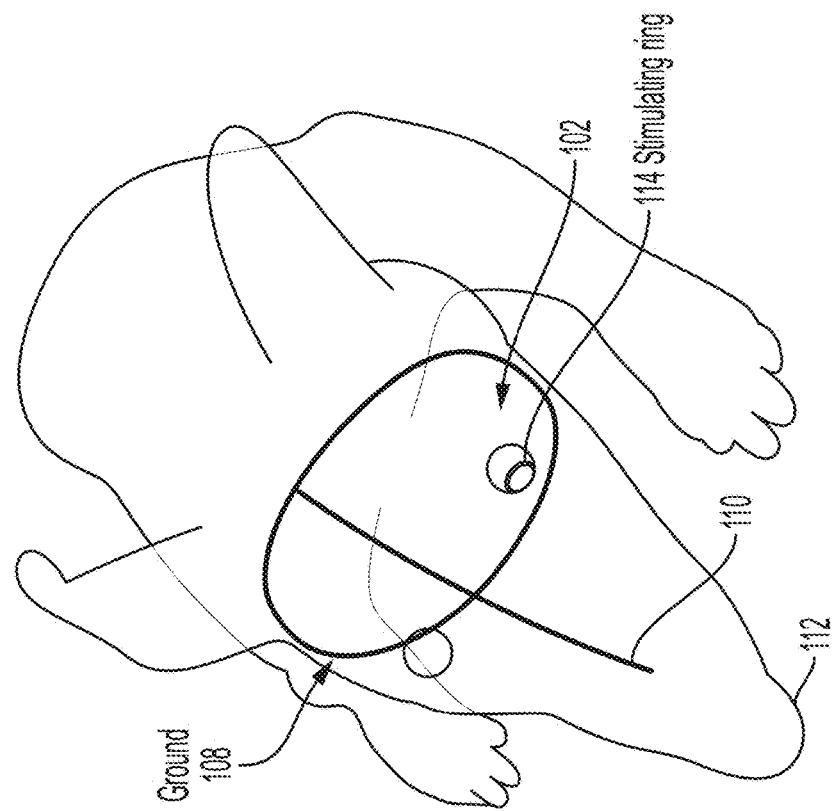
FIG. 2A

|  | Weeks | | | | | | |
| --- | --- | --- | --- | --- | --- | --- | --- |
|  | 1 | 2 | 3 | 4 | 5 | 6 | 7 |
| Anesthesia | X | X | X | X | X | X | X |
| OCT | X |  | X |  | X | X | X |
| FAF | X |  | X |  |  |  | X |
| Stimulation | X | X | X | X | X | X | X |
| Euthanasia |  |  |  |  |  |  | X |
| Histology |  |  |  |  |  |  | O |

X all cohorts   O Half cohorts

FIG. 5

| Number of Animals | Frequency (Hz) | Pulse width (ms) | Amplitude (µA) |
|---|---|---|---|
| 8 | 6 | 10 | 20 |
| 8 | 6 | 10 | 50 |
| 8 | 6 | 10 | 100 |
| 9 | NA | NA | Sham |

FIG. 7

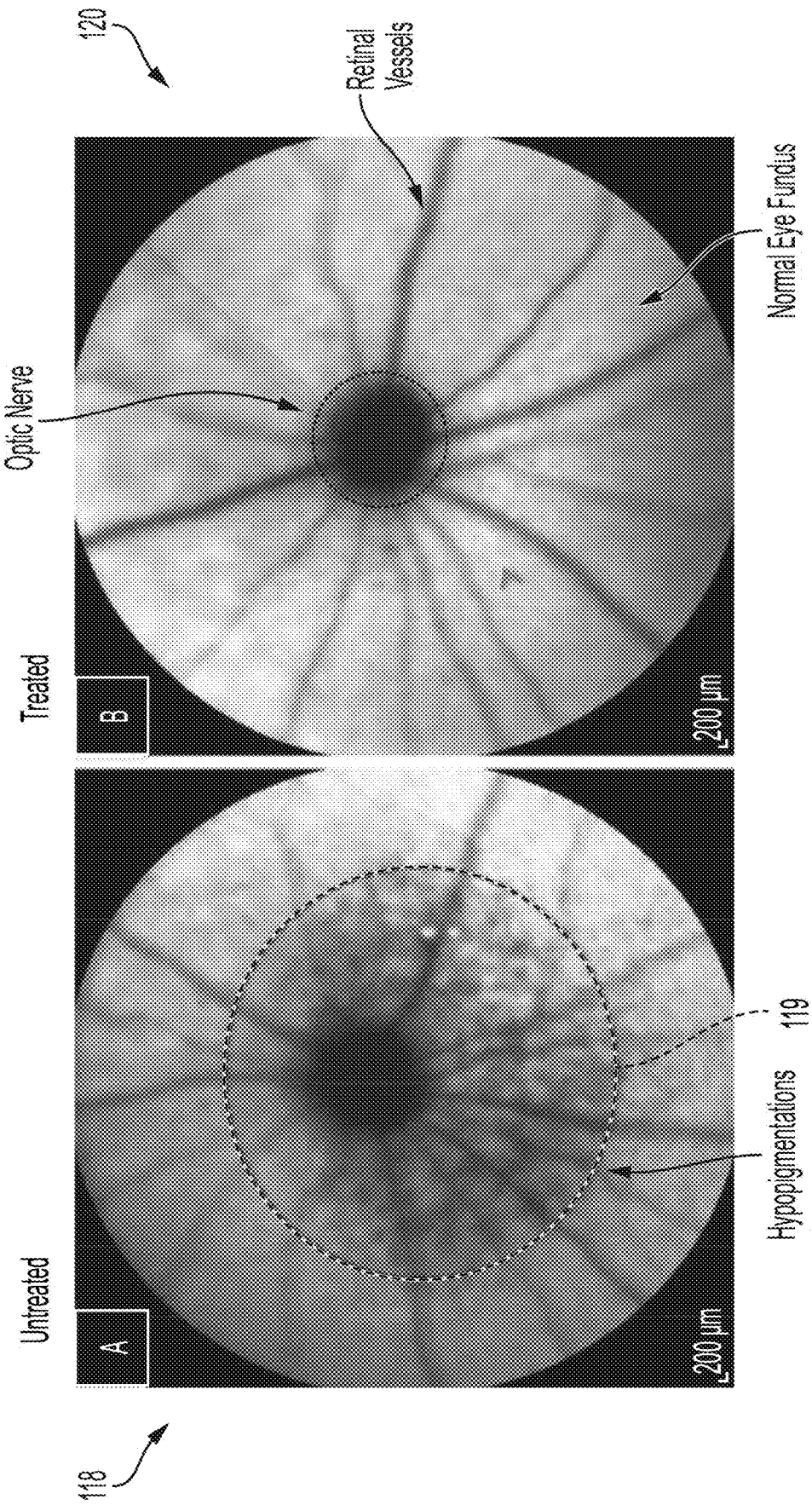

| PR Count | Sham | | 20uA | | 50uA | | 100uA | |
|---|---|---|---|---|---|---|---|---|
| | Non-Treated | Treated | Non-Treated | Treated | Non-Treated | Treated | Non-Treated | Treated |
| Average | 575 | 556 | 464.7 | 487.7 | 375 | 453 | 516.3 | 714 |
| SE | 7.78 | 15.45 | 7.93 | 97.5 | 16.04 | 24.48 | 27.76 | 36.55 |
| Improvement Treated Vs. Non Treated | 0% | | 4.95% | | 20.8% | | 38.2% | |
| P Value | 0.2036 | | 0.6794 | | 0.0548 | | 0.0091 | |

FIG. 12

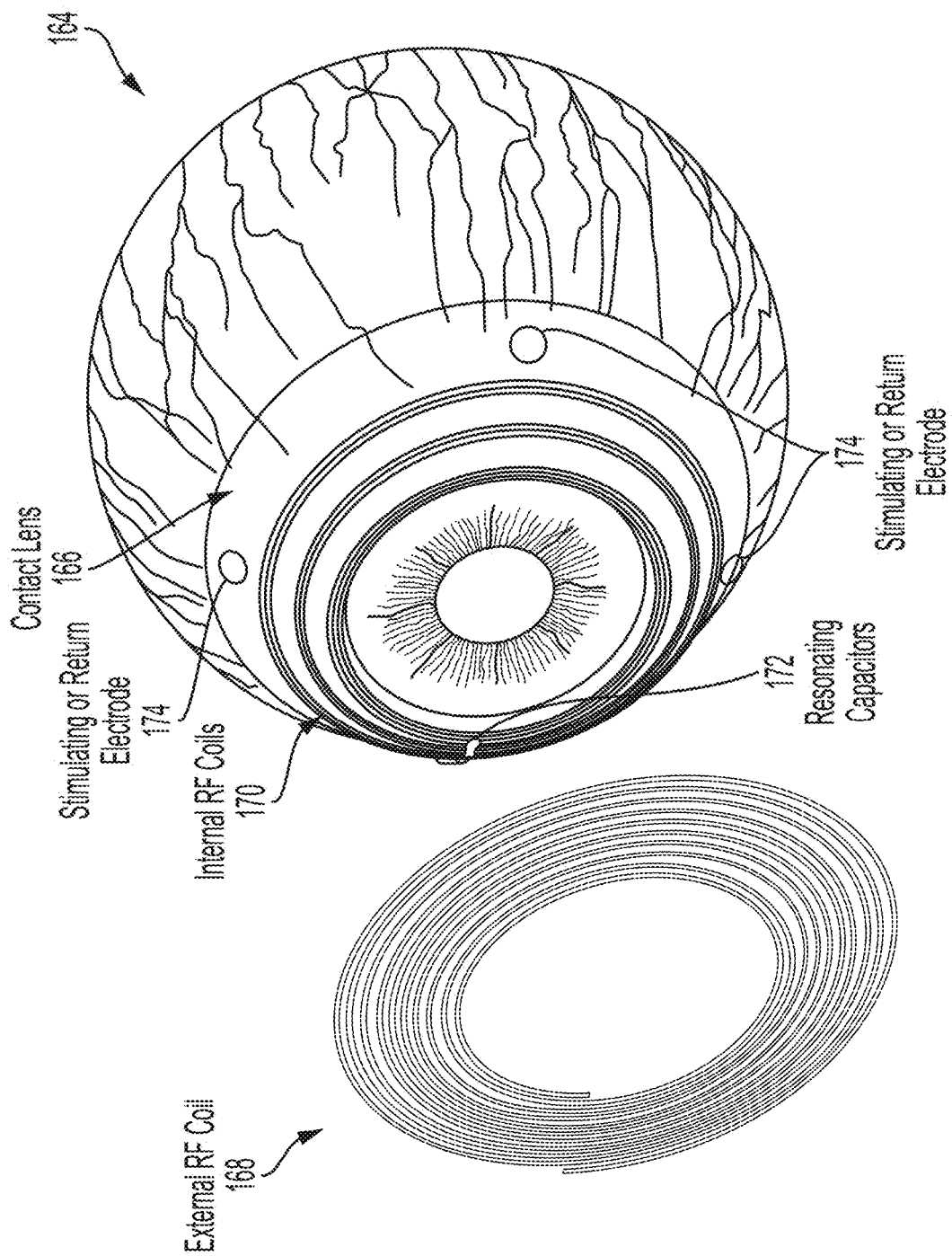

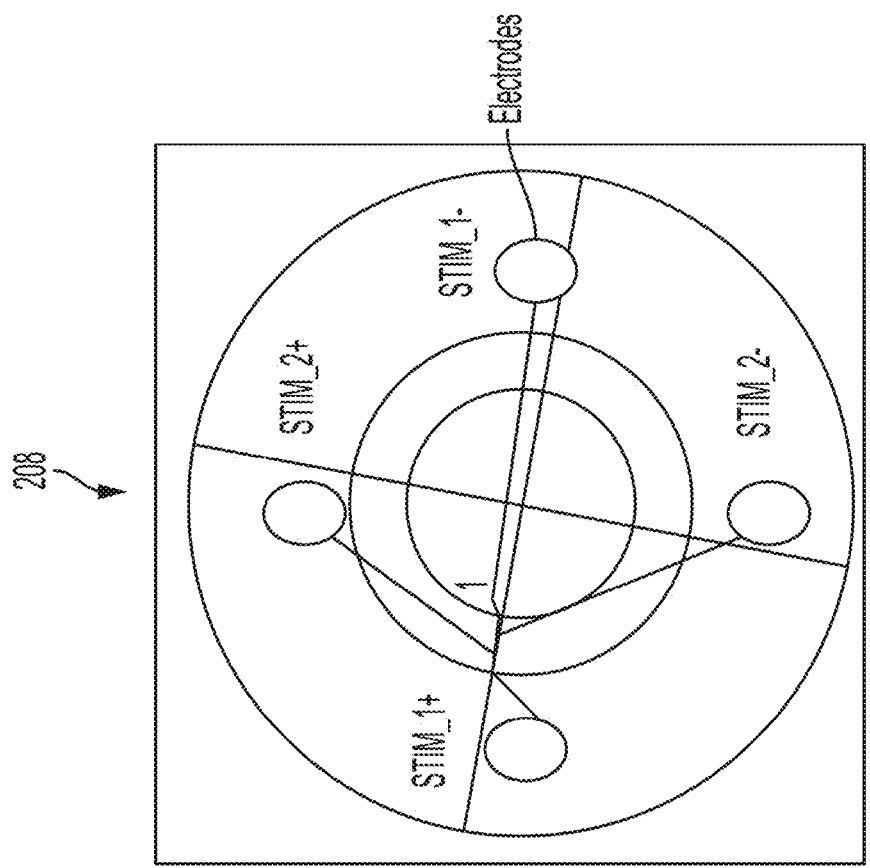
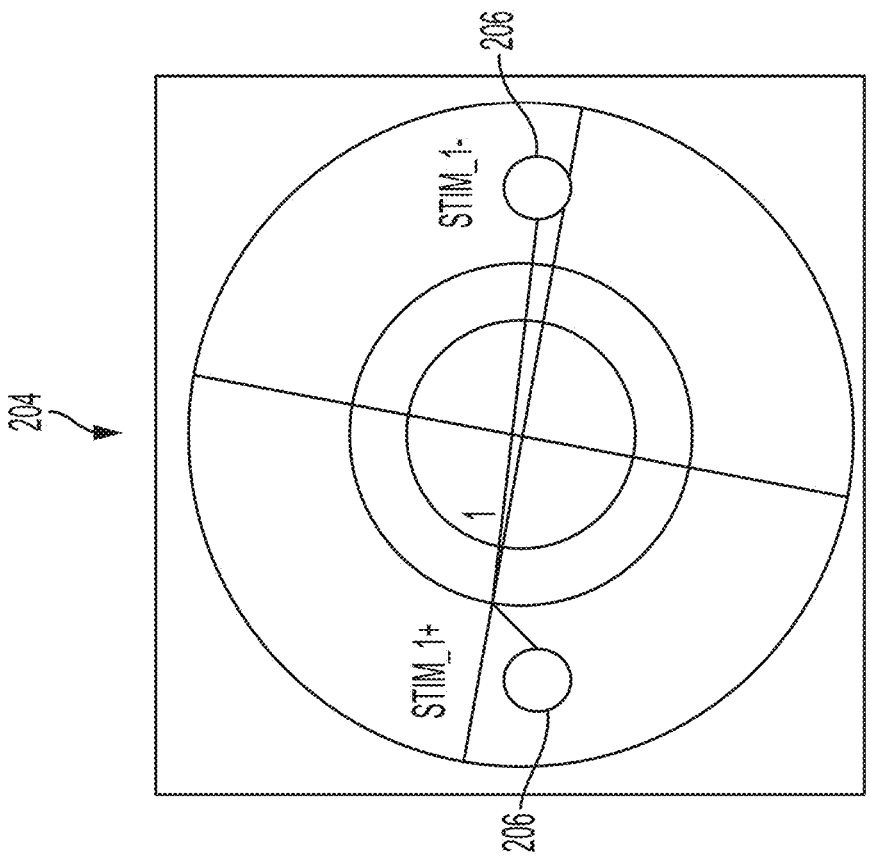
FIG. 30A
FIG. 30B

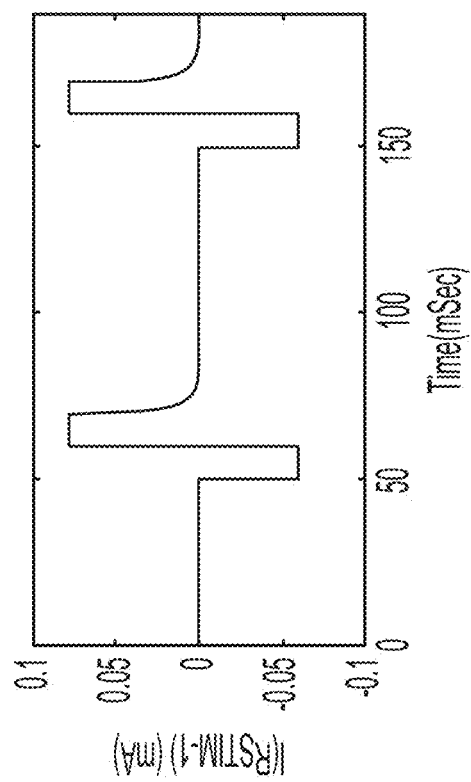
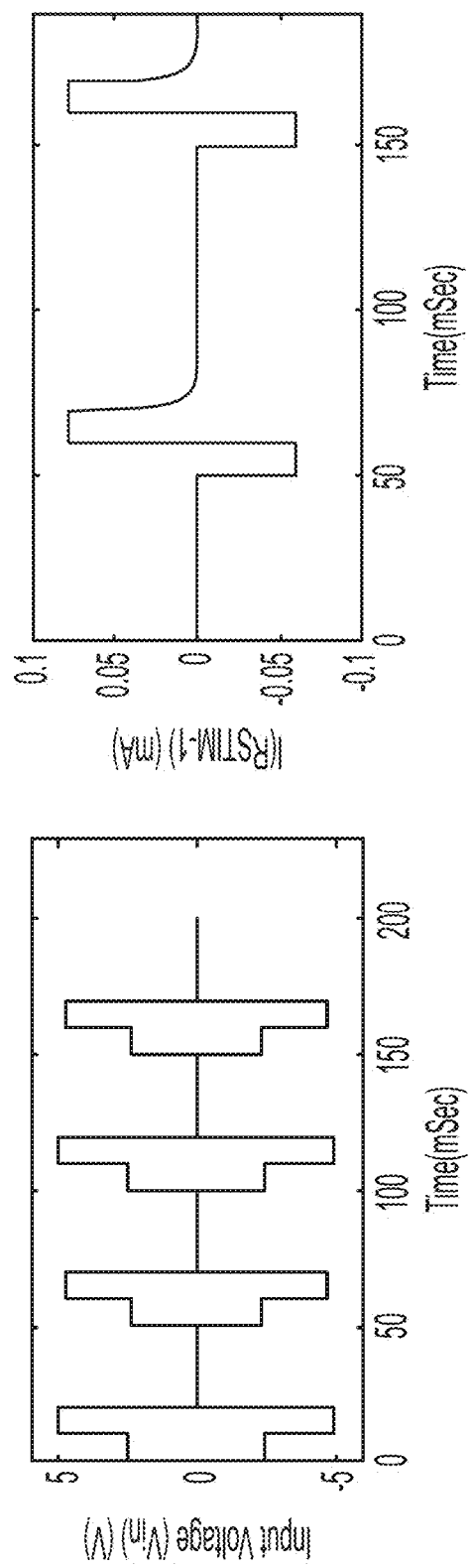
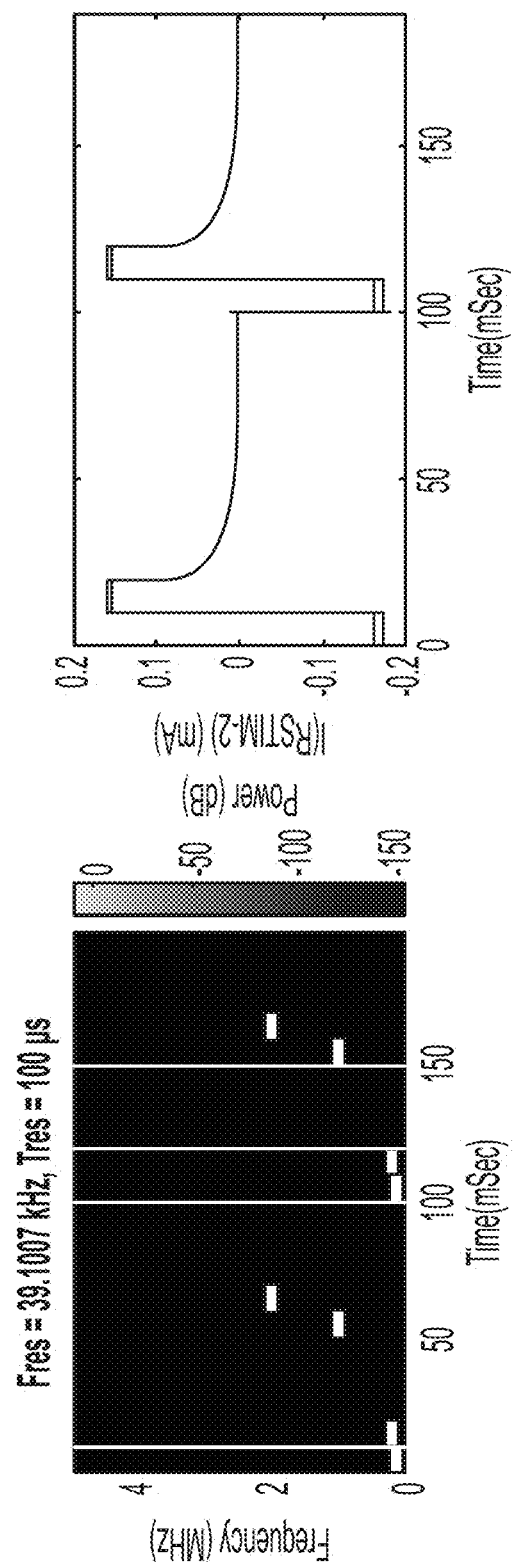
FIG. 32C
FIG. 32D
FIG. 32A
FIG. 32B

BIOELECTRONIC LENS (E-LENS) SYSTEM FOR ELECTRICAL STIMULATION AND NEUROPROTECTION OF THE RETINA

CROSS REFERENCE TO RELATED APPLICATIONS

This application claims the benefit and priority of U.S. Provisional Application Ser. No. 63/155,715, entitled "Bioelectronic Lens (E-lens) System For Electrical Stimulation And Neuroprotection Of The Retina," filed on Mar. 2, 2021, and U.S. Provisional Application Ser. No. 63/277,980, entitled "Bioelectronic Lens (E-lens) System For Electrical Stimulation And Neuroprotection Of The Retina," filed on Nov. 10, 2021, the contents of which are hereby incorporated by reference in their entirety herein.

STATEMENT AS TO FEDERALLY SPONSORED RESEARCH

This invention was made with government support under the grant Emerging Frontiers and Multidisciplinary Activities (EFMA) 1933394 awarded by the National Science Foundation (NSF) Emerging Frontiers in Research and Innovation (EFRI). The government has certain rights in this invention.

DESCRIPTION OF THE RELATED ART

Neurodegenerative diseases including retinal degenerations such as Retinitis Pigmentosa (RP), Age-Related Macular Degeneration (AMD), and glaucoma (POAG) are multiphase conditions characterized by unrelenting neuronal death (photoreceptor loss in RP and AMD and ganglion cell loss in POAG). Neuronal rewiring, reprogramming, and migration may manifest early in most of these conditions. These neurodegenerations are prevalent and blinding conditions alone account for a significant part of the estimated US$139 billion annual economic burden of vision disorders in the U.S. A number of mechanisms have been identified as to why neuronal death occurs in these different retinal blinding disorders (e.g., genetic mutations in RP, lipid metabolism abnormalities and inflammation in AMD, and elevated intraocular pressure in POAG to name a few). Although treatments to ameliorate these conditions exist, for many afflicted, there is no cure. Thus, there is a need for improved treatment of these conditions.

SUMMARY

What is described is a bioelectronic lens (E-lens) system with the ability to induce neuroprotective changes in neurons, in particular the retina. The designed stimulation strategies establish electrical gradients across existing but diseased/degenerating neurons, which may be used as therapeutic treatments to slow down, stop, or potentially even reverse progressive neurodegenerative disease. The electrical stimulation setup is designed such that safe and effective delivery of electric fields in the retina is assured. The system includes a stimulating electrode placed on the sclera or cornea or on the eyelid and a reference electrode designed such that electric fields in the retina are effectively induced and better reach the subthreshold currents of the targeted retinal neurons. The configuration of the stimulating electrode is designed such that the safety of the electrical stimulation is maximized. The Admittance Method (AM)/NEURON computational platform has been utilized to compute the induced electric fields distribution and further analyze the response of retinal neurons to the designed electrical stimulation parameters. The models of retinal neurons such retinal ganglion cells (RGCs) and bipolar cells (BCs) have been developed based on the experimental data and available modeling data from literature. There has been no systematic research conducting the most effective electrical stimulation approach for selective induction of therapeutic treatments in the retinal neurons. The systems disclosed herein are minimally invasive, cost effective, ubiquitously available, and adaptive technologies capable of rigorously exploring, recording, and controlling neural circuits, from a molecular to whole-system level over extended periods of time.

The components of this disclosure include: 1) A large-scale human and rat segmented models including the finer structures of the eye as well as micro-scale modeling of retinal layers and connectome; 2) Analyzing, for the first time, the response of retinal neurons to ocular electrical stimulation; 3) Designing the best electrodes configuration and placement to maximize the induce electric fields in the retina and further control the level of induced fields in different layers of the retina; 4) Designing the most effective electrical stimulation waveform to induce directed electric fields and better target the outer layers of the retina such bipolar cells, which are mostly affected at the early stages of retinal degeneration.

BRIEF DESCRIPTION OF THE DRAWINGS

Systems, methods, features, and advantages of the present disclosure will be apparent to one skilled in the art upon examination of the following figures and detailed description. Component parts shown in the drawings are not necessarily to scale and may be exaggerated to better illustrate different features of the present disclosure.

FIG. 2A illustrates an electrical stimulation setup having a ground electrode wrapped around the eye with a wire extended to the nose according to an aspect of the present disclosure.

FIG. 2B illustrates a slice of the voltage distribution in the eye and the brain according to an aspect of the present disclosure.

FIG. 2C illustrates voltage distributed in the central retinal coupled with models of retinal neurons, retinal ganglion cells, and bipolar cells according to an aspect of the present disclosure.

FIG. 5 illustrates procedures performed in animals during a 7-week experiment according to an aspect of the present disclosure.

FIG. 7 illustrates stimulation parameters and the number of animals that were included for each stimulation parameter set according to an aspect of the present disclosure.

FIG. 8A illustrates a non-treated eye where hypopigmentations are observed inside a dotted circle according to an aspect of the present disclosure.

FIG. 8B illustrates a treated eye where early stages of degeneration are observed as sparse hyperpigmented spots according to an aspect of the present disclosure.

FIG. 12 illustrates photoreceptor counts acquired from all stimulated and sham groups according to an aspect of the present disclosure.

FIG. 21 illustrates a wireless E-lens system according to an aspect of the present disclosure.

FIG. 30A illustrates a contact lens on the retina with a single stimulation electrode according to an aspect of the present disclosure.

FIG. 30B illustrates a contact lens on the retina with two stimulation electrodes according to an aspect of the present disclosure.

FIG. 32A illustrates a frequency graph according to an aspect of the present disclosure.

FIG. 32B illustrates an input voltage waveform to independently control the two electrodes wirelessly according to an aspect of the present disclosure.

FIG. 32C-illustrates a load current flowing in a load of the circuit of FIG. 31 according to an aspect of the present disclosure.

FIG. 32D illustrates a load current flowing in a load of the circuit of FIG. 31 according to an aspect of the present disclosure.

DETAILED DESCRIPTION

The systems and methods described herein show that non-invasive electrical stimulation may control the induced electric fields in neurons with implications for neuroprotection. The systems and methods described herein allow for systematic, and therefore more reliable and reproducible, retinal and central nervous system neuroprotection.

The systems and methods described herein use a designed electrical stimulation strategy to direct the induced voltage gradients towards the outer retinal neurons, which are influenced at the early stages of retinal degeneration, thereby slowing the progression of neural degeneration. The pathological mechanisms in prevalent retinal disease (e.g., photoreceptor degeneration—such as Retinitis Pigmentosa (RP) and Age-Related Macular Degeneration (AMD)—or Primary Open Angle Glaucoma (POAG)) are becoming better understood. In spite of this, because of the more than 100 mutations that cause RP, for example, curing this family of mutations beyond the one-off gene therapy success as seen in the rare condition of Leber congenital amaurosis (RPE65 mutation) has been a daunting task. Similarly, intraocular pressure control becomes more difficult with the progression of glaucoma and neuroprotection is needed.

Previous uses of electrical and magnetic stimulation of the retina have been limited to rehabilitative devices, often utilized to bypass damaged neurons for partial vision restoration in patients with near total blindness. The systems and methods described herein introduce a different approach through a paradigm shift to prevent or delay neuronal loss experienced in incurable diseases such as RP, AMD, and POAG. Controlled electromagnetic fields may modulate functional and morphological neural alterations by exploiting transcriptional regulation of gene expression potentiated by chromatin packing and epigenomic remodeling. This approach may be used both early in the course of retinal diseases to slow down progression and late in the disease, complementing pharmacological and surgical therapies. It is important to note, that the form of electrical stimulation used herein is very different and not the type used in neural prosthetics which use electrical stimulation to bypass damaged photoreceptors and activate remaining retinal neurons to restore visual function.

Transcorneal electrical stimulation (TES) may alter the gene expression and reduce the rate of death of photoreceptors as well as delay the progression of retinal degenerative diseases. Other invasive methods may have a variety of effects on the retina, ranging from promotion of the survival of the axotomized retinal ganglion cells to rescue of photoreceptors. However, there is insufficient characterization of the causes responsible for these effects and limited understanding of the fundamental mechanisms.

Figure 1:
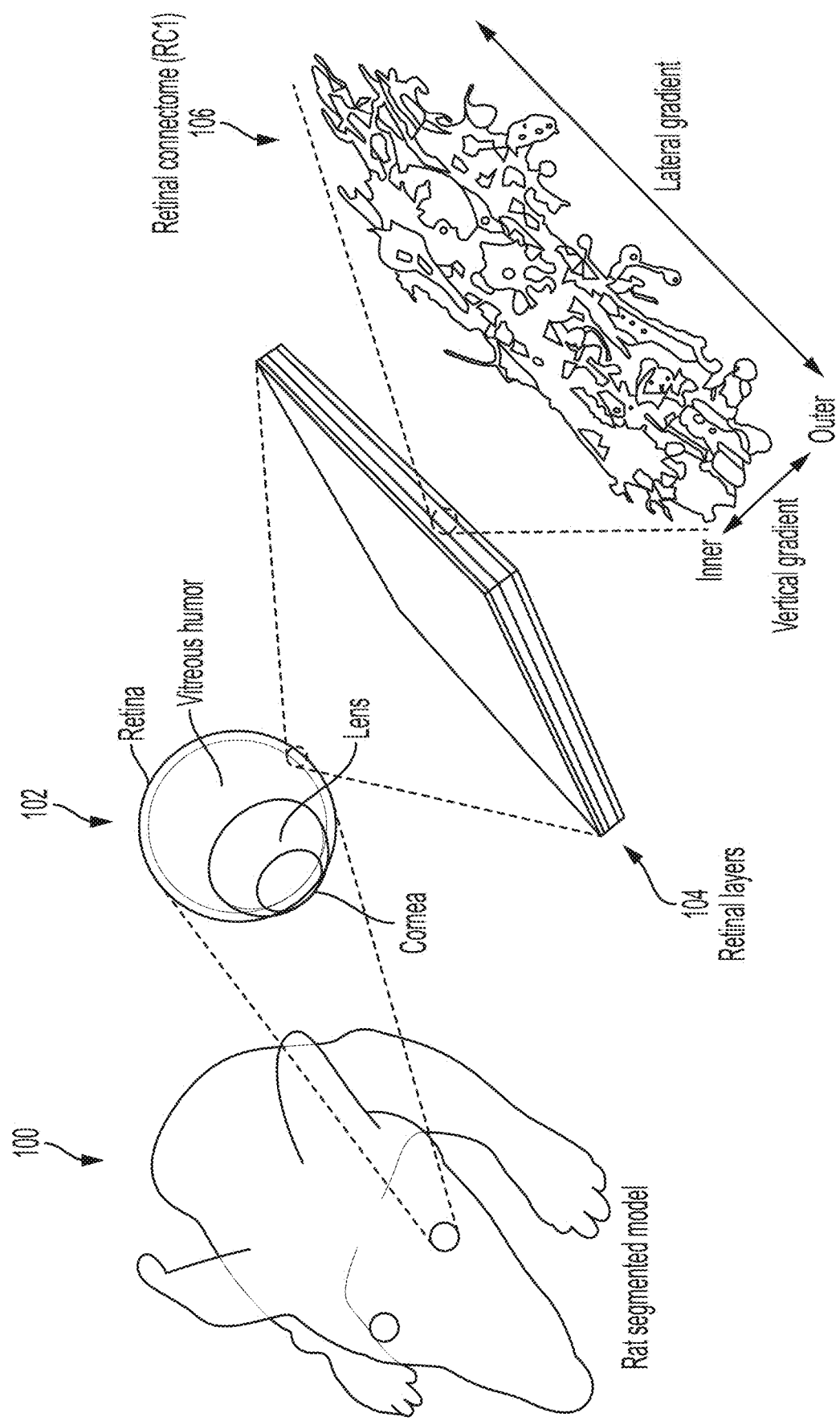
FIG. 1 illustrates a multiscale Admittance Method/NEURON computational platform capable of constructing a large-scale rat voxel model, fine details of the eye, retinal layers, and cellular-level modeling of retinal network including retinal ganglion cells and bipolar cells according to an aspect of the present disclosure.

FIG. 1 illustrates a multiscale Admittance Method/NEURON computational platform capable of constructing a large-scale rat voxel model 100, fine details of the eye 102, retinal layers 104, a retinal connectome 106, and cellular-level modeling of retinal network including retinal ganglion cells and bipolar cells.

FIG. 2A illustrates an electrical stimulation setup having a ground electrode 108 wrapped around the eye 102 with a wire 110 extended into the nose 112 and a stimulating ring 114. The ground configuration is designed such that the voltage distribution is focalized near the eyes 102 and the electric field gradient (activation function) is maximized along the thickness of the retina. The activating function is a mathematical prediction of neural activation from extracellular voltages derived from external electrical stimulation. The minimum resolution of rat voxel model was set to 160 μm and a maximum merged element size of 64 voxels was applied. The final computational model is composed of approximately 400 million computational cells.

FIG. 2B illustrates a slice of the voltage distribution in the eye and the brain. Resulting extracellular voltages induced in the retina tissue from the AM model were applied to multi-compartment models of neurons using NEURON simulations, and then neuronal responses of the developed RGCs and BCs were recorded. Therefore, to save the computation time of NEURON simulations and increase the spatial resolution of the resulting voltages, the central retinal was analyzed as shown in FIG. 2C, which illustrates voltage distributed in the central retinal coupled with models of retinal neurons, retinal ganglion cells, and bipolar cells.

Figures 3A, 3B:
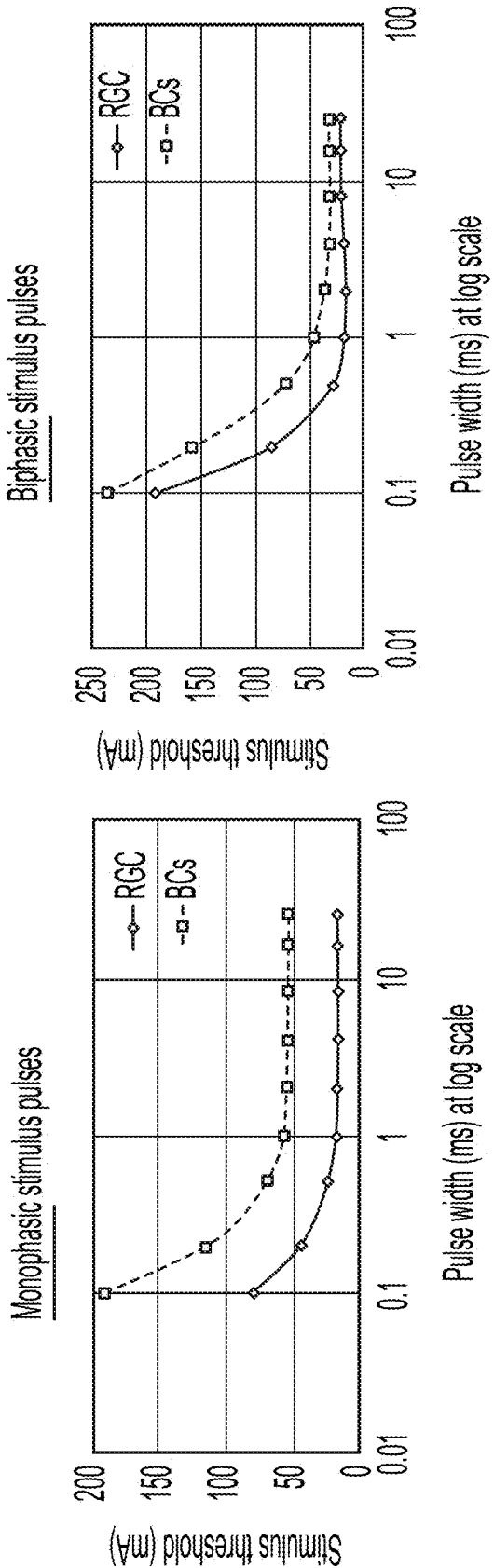
FIG. 3A illustrates strength-duration curves of retinal ganglion cells and bipolar cells due to monophasic stimulus pulses according to an aspect of the present disclosure.
FIG. 3B illustrates strength-duration curves of retinal ganglion cells and bipolar cells due to symmetric charge-balanced biphasic stimulus pulses according to an aspect of the present disclosure.

FIG. 3A illustrates strength-duration curves of retinal ganglion cells and bipolar cells due to monophasic stimulus pulses. FIG. 3B illustrates strength-duration curves of retinal ganglion cells and bipolar cells due to symmetric charge-balanced biphasic stimulus pulses. Long biphasic stimulus pulses have significantly reduced the subthreshold current of retinal bipolar cells relative to monophasic pulses. Further, long pulse durations have shown to decrease the differential stimulus threshold between the RGCs and BCs, thereby increasing the chance for targeting the outer retinal neurons for therapeutic treatments and slowing down the retinal degeneration progression.

Figure 4B:
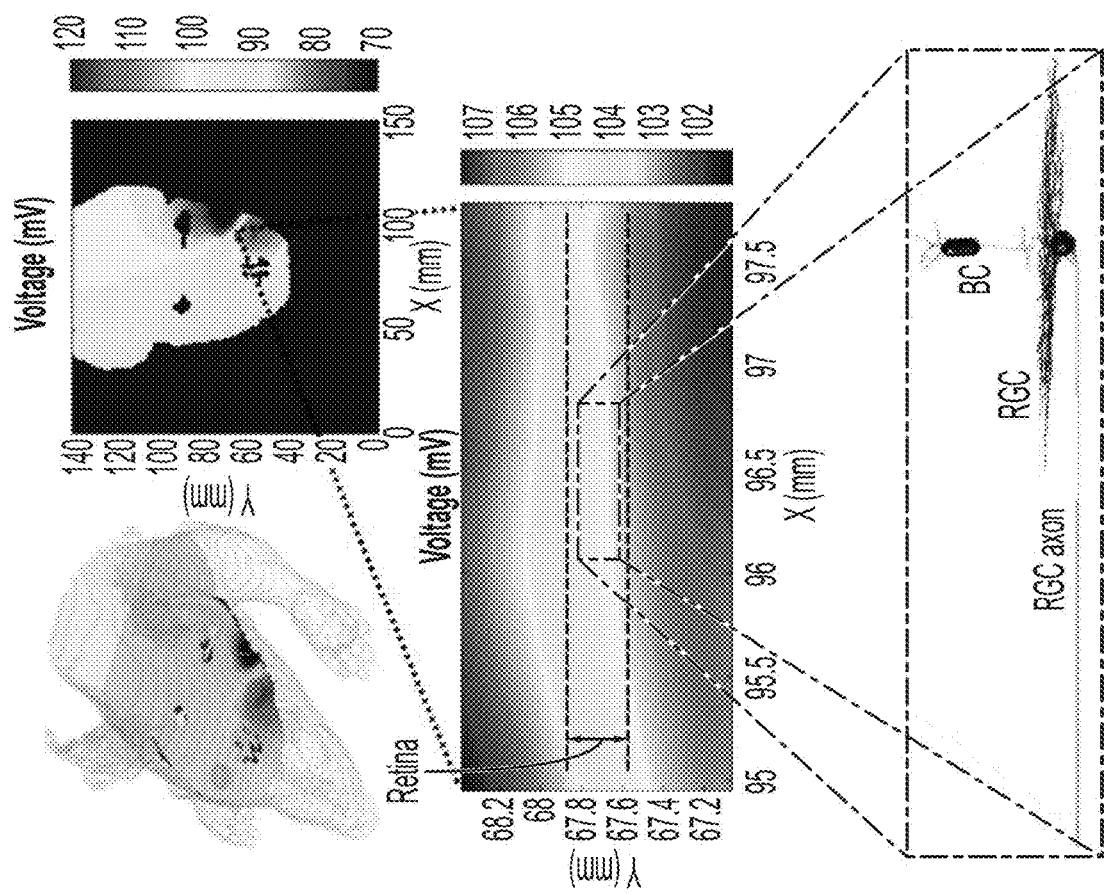
FIG. 4B illustrates a numerical simulation of the system according to an aspect of the present disclosure.
Figure 4A:
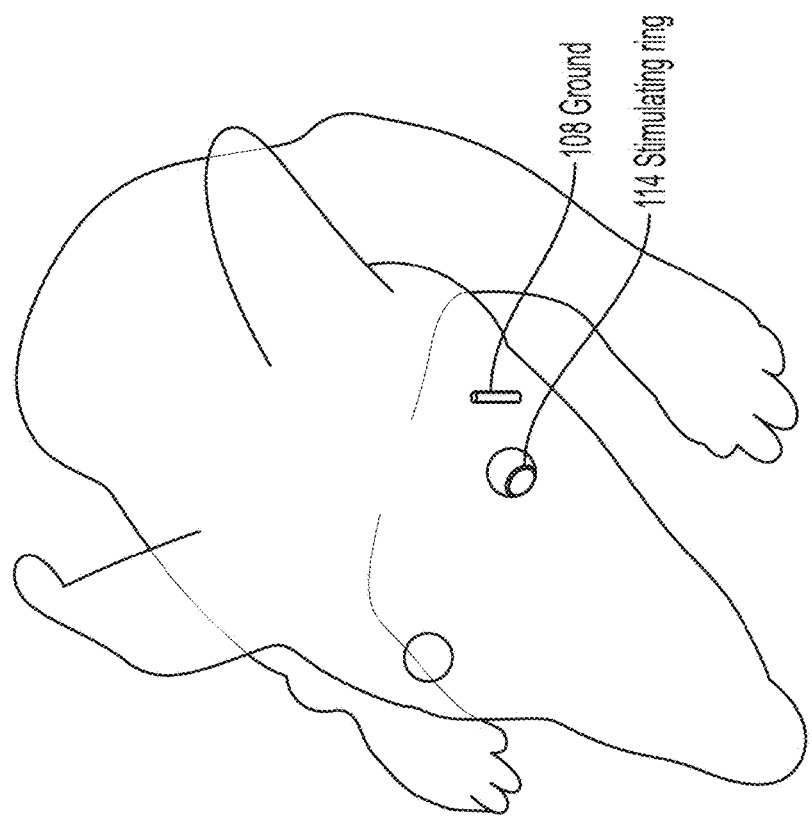
FIG. 4A illustrates an electrical stimulation setup according to an aspect of the present disclosure.

An alternative ground configuration and placement have been proposed as well to achieve similar induced electric fields in the retina. FIG. 4A illustrates the transcorneal electrical stimulation setup placing the needle ground electrode 108 on the temporal site of the stimulating ring 114 placed on the sclera. The new ground placement with relatively simpler implementation for electrophysiological and clinical experiments has been shown to induce electric fields along the retinal thickness similarly to the previous ground configuration shown in the numerical simulation illustrated in FIG. 4B. The setup allows more effective targeting of the outer retinal neuron due to the increased voltage gradients along the thickness of the retina and therefore greater chance for neuroprotective effects, reinnervation, and preserving the healthy retinal neurons.

FIG. 5 illustrates procedures performed in animals during a 7-week in-vivo experiment. The Royal College of Surgeon (RCS) rats were used for assessing the beneficial effects of electrical stimulation. RCS rats have an inherited retinal degeneration making them a great model to study how to preserve and restore vision. All animals were maintained on a daily 12 h light/day cycle prior experiments. All procedures conformed to the Guide for Care and Use of Laboratory Animals (National Institute of Health).

RCS rats 20-60 days old were used for all experiments. Stimulation was performed in only one of each animal (n=33). Body temperature was regulated and maintained at 37° C. with an electric heating pad. Heart rate and respiration was monitored throughout the experiment. Animals were stimulated once a week in the right eye for two hours beginning at age of postnatal day 20 (P20). Each rat received one stimulation session weekly until reaching the age of p60 completing a total of 6 stimulation sessions. Stimulation was performed at P21, P28, P35, P42, P49 and P56. Animals underwent Fundus Autofluorescence (FAF) and Coherence Tomography (OCT) imaging at P21, P35, P49 and P60 (FIG. 5). OCT imaging was used to monitor the changes in retinal layer thickness, including the Outer Nuclear Layer. FAF imaging was used to evaluate RPE health and disease progression by assessing the hypofluorescent and hypopigmented areas of the whole retina.

A ring-shaped electrode similar to the ring 114 of the embodiment of FIG. 4A (4 mm in diameter) was placed on the sclera (right eye) and used as the stimulating electrode. An electrode was placed temporally of the stimulated eye as a ground electrode. Charge-balanced, cathodic first, biphasic pulses with a pulse width of 10 ms, and no interphase gap were used for all stimulating groups.

Figure 6:
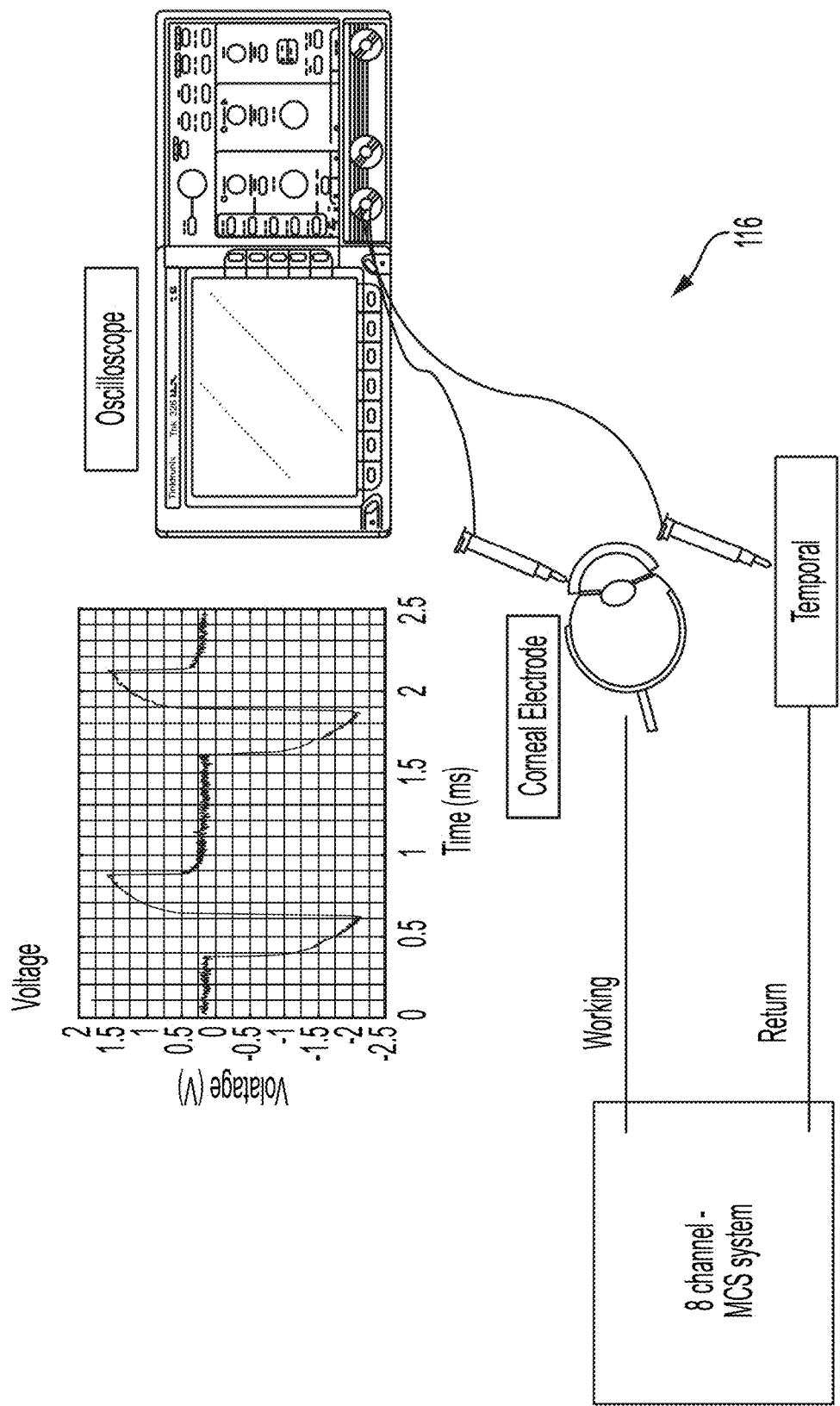
FIG. 6 illustrates an experimental setup schematic that was used for the electrical stimulation experiments according to an aspect of the present disclosure.

FIG. 6 illustrates a schematic of the experimental setup 116 that was used for the electrical stimulation experiments. FIG. 7 illustrates the stimulation parameters and the number of animals that were included for each stimulation parameter set. The frequency was set at 6 Hz and the current amplitudes of 20 μA (n=8), 50 μA (n=8), and 100 μA (n=8) were tested. Sham group (n=9) had the ring-shaped electrode placed on the right sclera and kept in place for 2 hours without any stimulation given. Histology was performed using Hematoxylin and Eosin stain (H&E) and photoreceptor count (PR) was done in both treated and untreated eyes.

FIG. 8A illustrates a non-treated eye 118 where hypopigmentations are observed inside a dotted circle 119. FIG. 8B illustrates a treated eye 120 where early stages of degeneration are observed as sparse hyperpigmented spots. FAF imaging was evaluated in order to assess the health of the whole retina and the disease progression. Progression of the disease may be evaluated by monitoring the amount of hyperpigmentations and hypopigmentations covering the retinal area. The first stages of degeneration may be observed with hyperpigmented spots, but while the diseases progress, hypopigmentations may be observed. The more hypopigmentations covering the area, the more advanced is the disease. FAF images were visually analyzed. It was observed that for the sham and 20 μA groups the disease progressed at a similar and steady rate in both treated eye 118 and non-treated eye 120. On the contrary, at 50 μA and 100 μA the rate at which the disease was progressing was reduced in the treated eye 118 compared to the untreated eye 120.

Figures 9A, 9B, 9C:
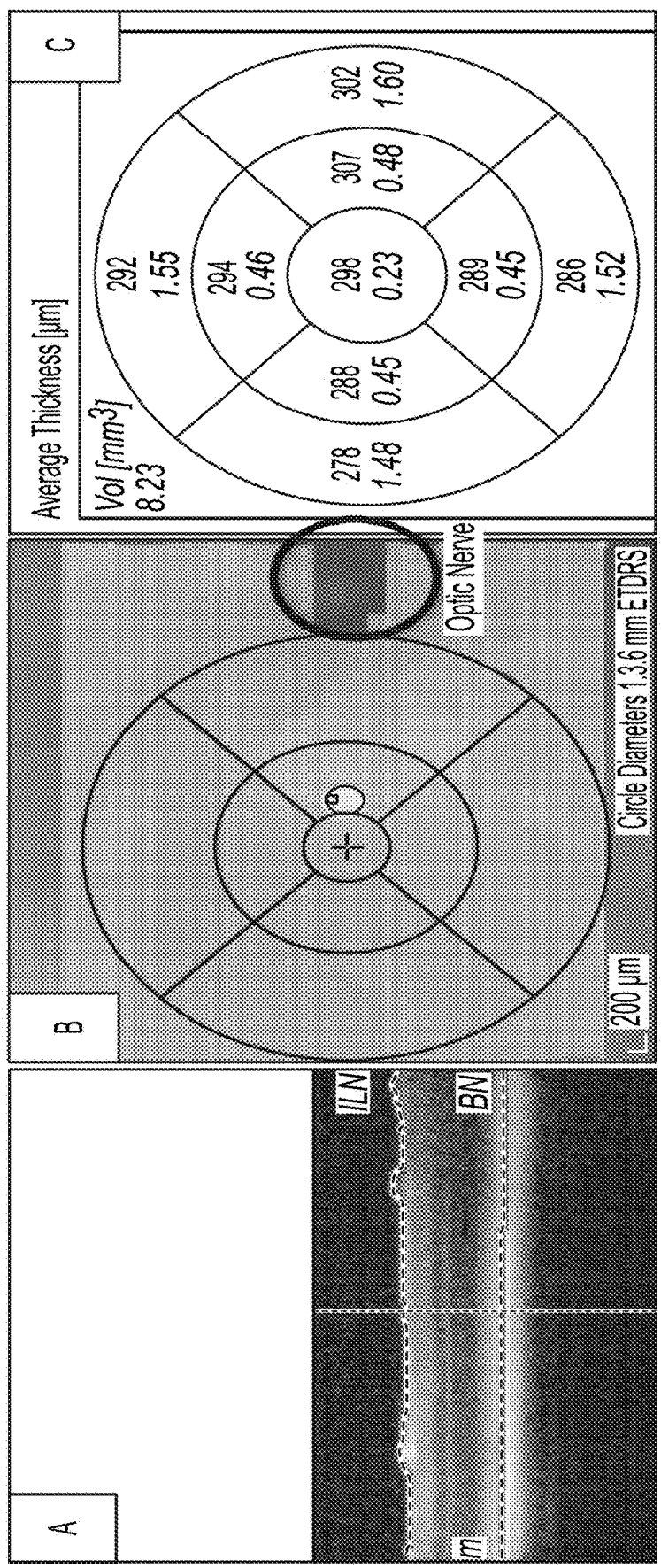
FIG. 9A illustrates volumes acquired from 60 individual retinal sections according to an aspect of the present disclosure.
FIG. 9B illustrates the optic nerve used as a landmark to analyze the same volume for all animals according to an aspect of the present disclosure.
FIG. 9C illustrates calculated retinal thicknesses according to an aspect of the present disclosure.

FIG. 9A illustrates volumes acquired from 60 individual retinal sections. FIG. 9B illustrates the optic nerve used as a landmark to analyze the same volume for all animals. FIG. 9C illustrates calculated retinal thicknesses. OCT imaging was used to monitor the changes in retinal layer thickness. Volume scans were taken every 30 ums and consists of 60 consecutive single scans. Volumes scans were images using the optic nerve as a landmark to ensure that the same area was analyzed for all animals. The spectralis software measures the thickness of the retinal between the two red lines as shown in the image below of each single scan and a volume thickness map is created. Retinal thickness was analyzed for both treated and non-treated eye. Data was analyzed using a computing software such as MATLAB or the like. A parametric paired t-test was performed to assess if the mean difference between treated and non-treated eye at p60 was significant.

Figure 10:
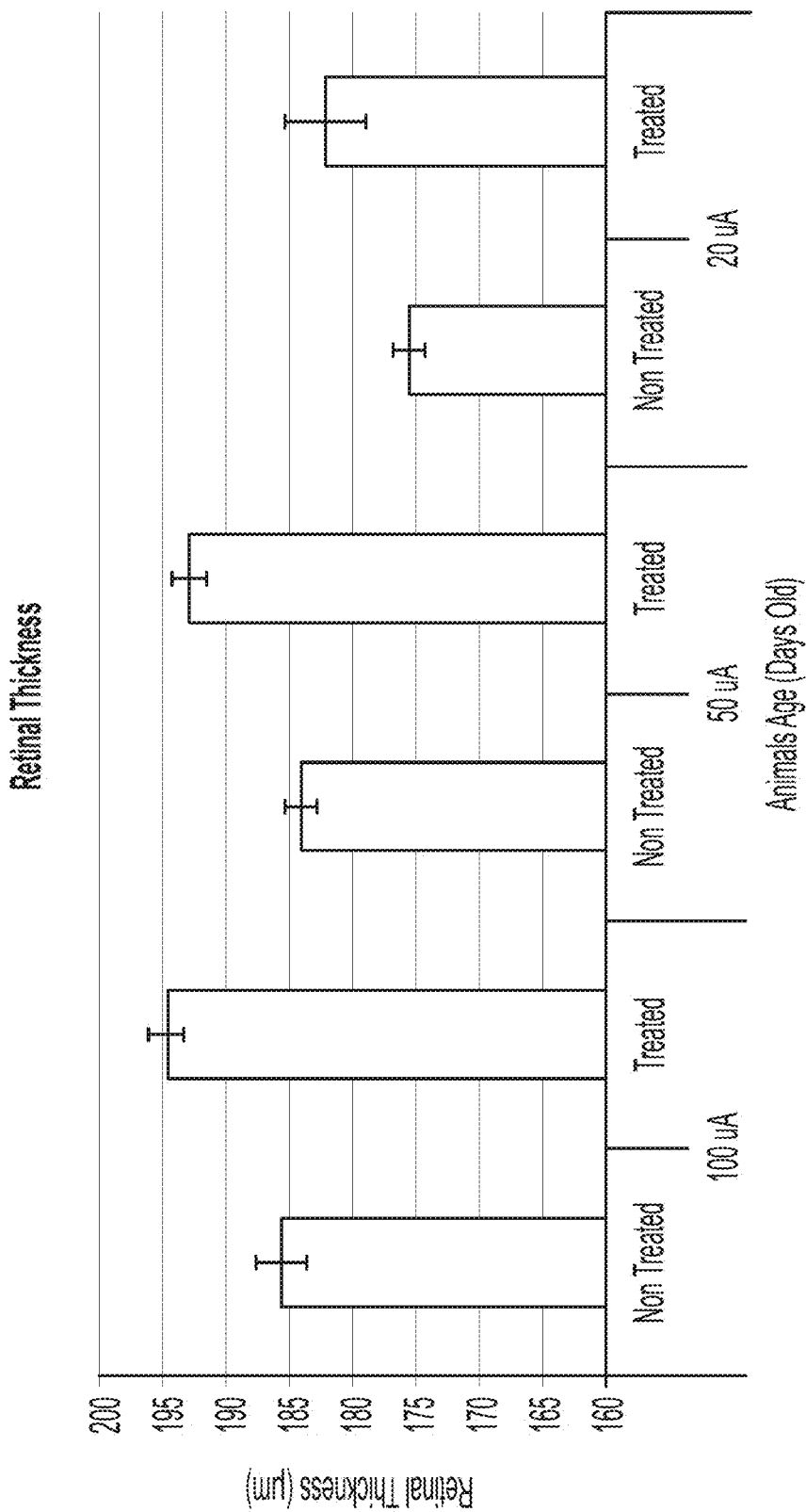
FIG. 10 illustrates a graph of retinal thicknesses from three stimulation groups stratified as non-treated vs. treated eyes according to an aspect of the present disclosure.

FIG. 10 illustrates a graph of retinal thicknesses from three stimulation groups stratified as non-treated vs. treated eyes. The observed differences between treated and non-treated within the sham and one stimulated at 20 μA was not statistically different (p=0.806 and p=0.242 respectively). However, the groups that were stimulated at 50 and 100 μA revealed a difference in retinal thickness that was statistically different between the treated and the non-treated eyes (p=0.005 and p=0.001, respectively).

Figure 11:
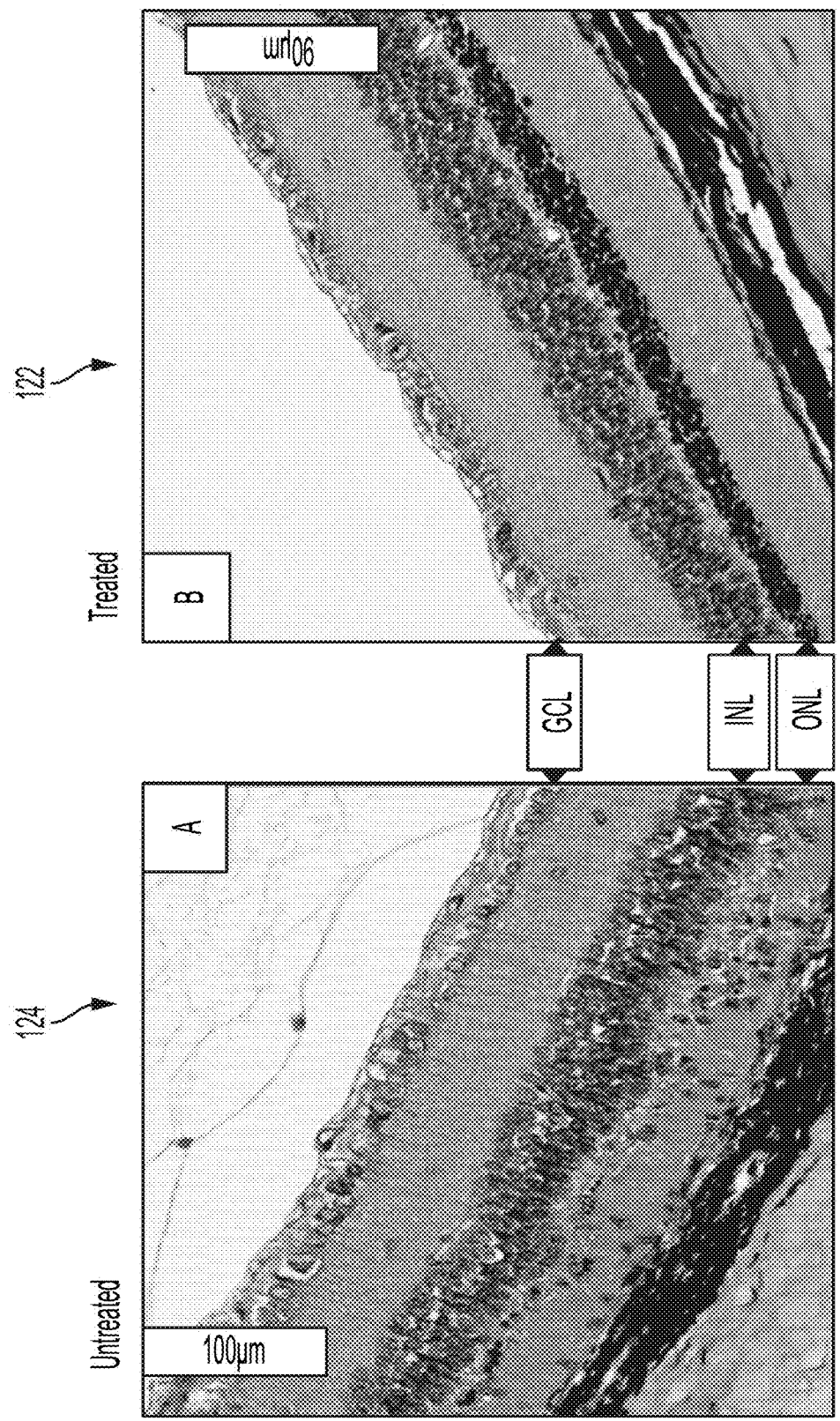
FIG. 11 illustrates cross section of histological slides comparing the treated versusthe non-treated eye of an animal stimulated from a 100 uA group according to an aspect of the present disclosure.

FIG. 11 illustrates cross section of histological slides comparing the treated eye 122 versus the non-treated eye 124 of an animal stimulated from a 100 uA group. Hematoxylin and eosin (H&E) staining was performed in half of the animals from each tested group (n=4). The histological slides were scanned, and photoreceptor counts were acquired from a 1 mm section located 1 mm away from the optic nerve in the inferior area of the retina. Photoreceptor counts were acquired from both the treated eye 122 and the non-treated eye 124.

FIG. 12 illustrates photoreceptor counts acquired from all stimulated and sham groups. The improvement was defined as the percent increase in photoreceptor count when comparing treated versus non-treated eyes. A parametric paired t-test was performed to assess if the mean difference between treated and non-treated eyes at p60 was significant. The mean photoreceptor count of treated versus non treated from the sham group did not show an increase in photoreceptor count when comparing both eyes, while the 20 μA group showed an improvement of 4.95%. Both of the aforementioned statistical tests did not show significant differences (p=0.2036 and p=0.6794, respectively). However, the 50 μA and 100 μA groups showed an improvement of 20.8% and 38.2% in photoreceptor count respectively, when comparing non-treated versus treated eyes, and the results proved to be nearly statistically significant for the former (p=0.0548) and statistically significant for the latter (p=0.0091).

Figure 13B:
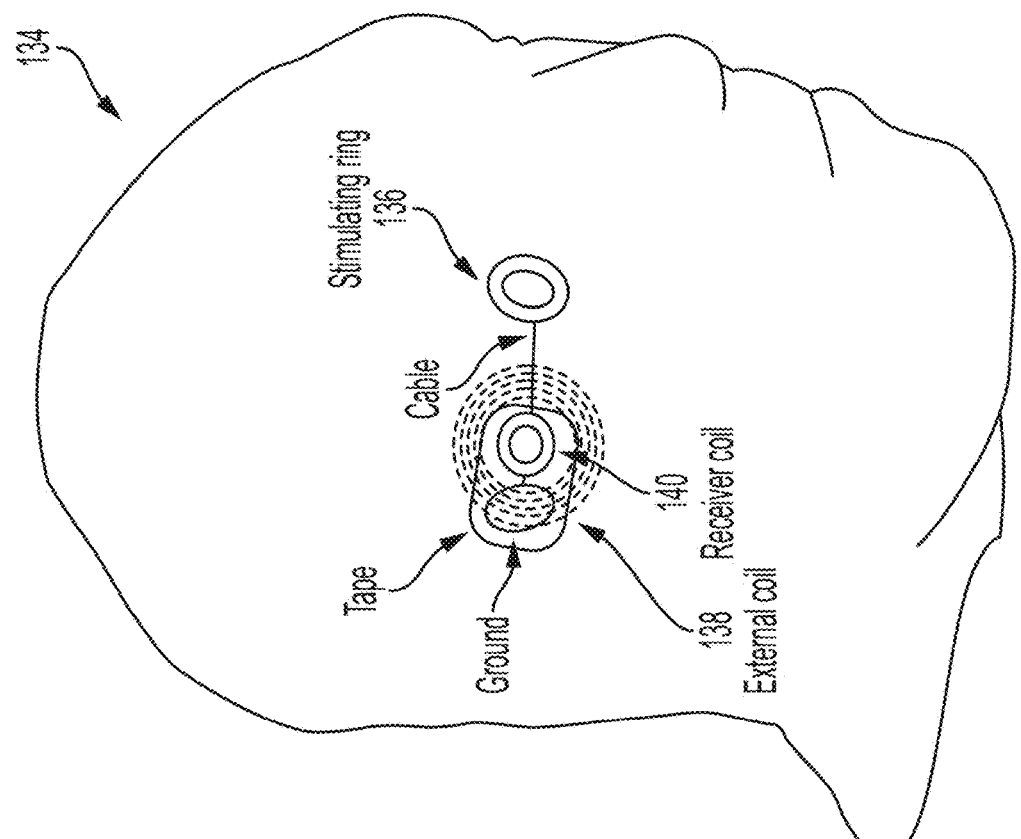
FIG. 13B illustrates an embodiment of a wired E-lens system according to an aspect of the present disclosure.
Figure 13A:
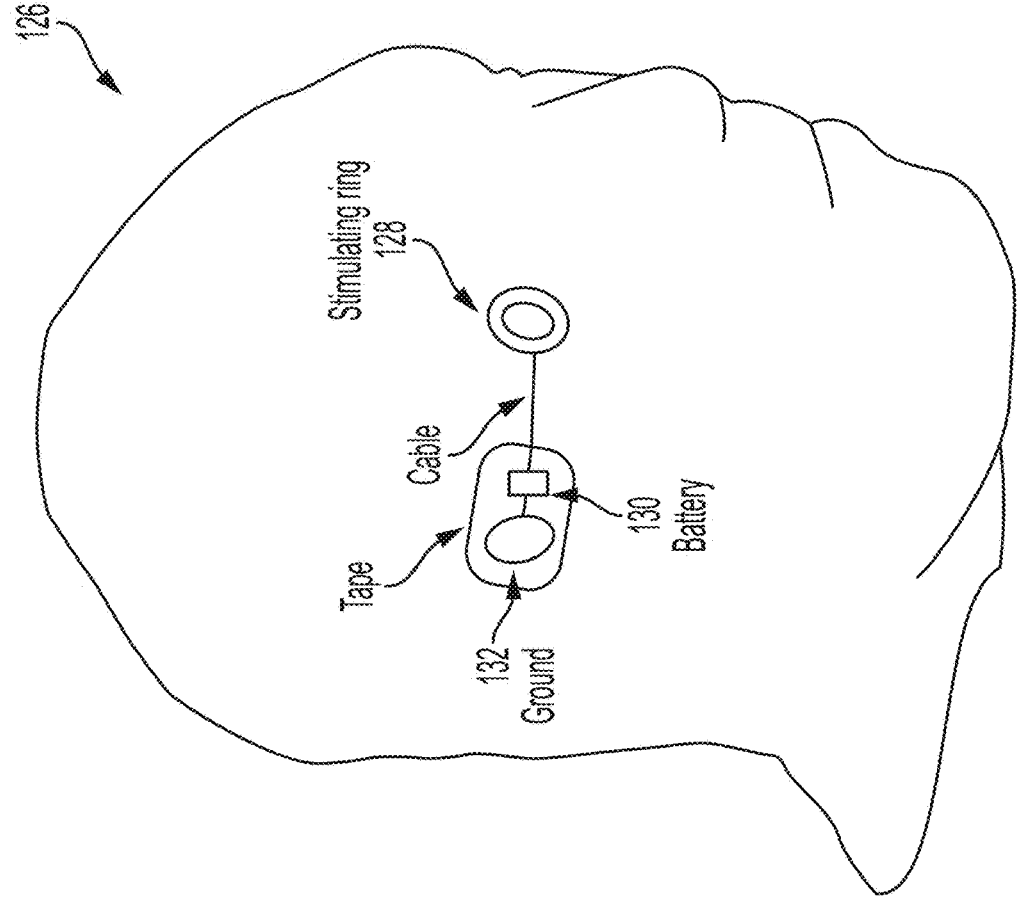
FIG. 13A illustrates an embodiment of a wired E-lens system according to an aspect of the present disclosure.

FIG. 13A illustrates an embodiment of a wired E-lens system 126 with a stimulating ring 128 on the sclera, cornea or eyelid, a battery 130, and a ground electrode 132 placed on the temporal area of the stimulated eye. Another embodiment of a wired E-lens system 134 is illustrated in FIG. 13B, having a wirelessly powered stimulating electrode 136 and a return current on the temporal side of the stimulated eye. An external coil 138 may be placed with a distance from a receiver coil 140 at the temporal region. The E-lens system 134 may include a battery or a wirelessly powered device to provide power supply and a desired stimulus waveform to the stimulating electrode.

Figure 14A:
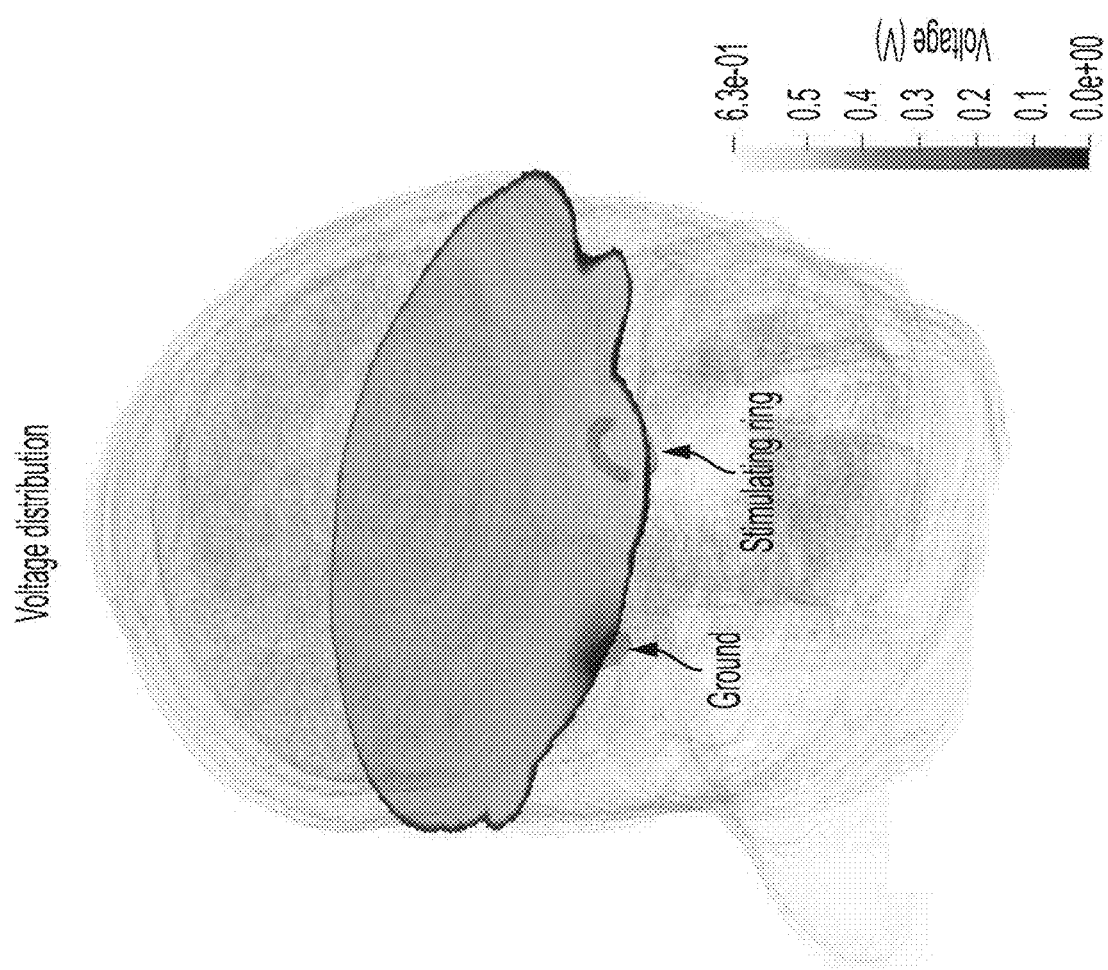
FIG. 14A illustrates a slice of the voltage distribution in the embodiments of FIGS. 13A-B according to an aspect of the present disclosure.
Figure 14B:
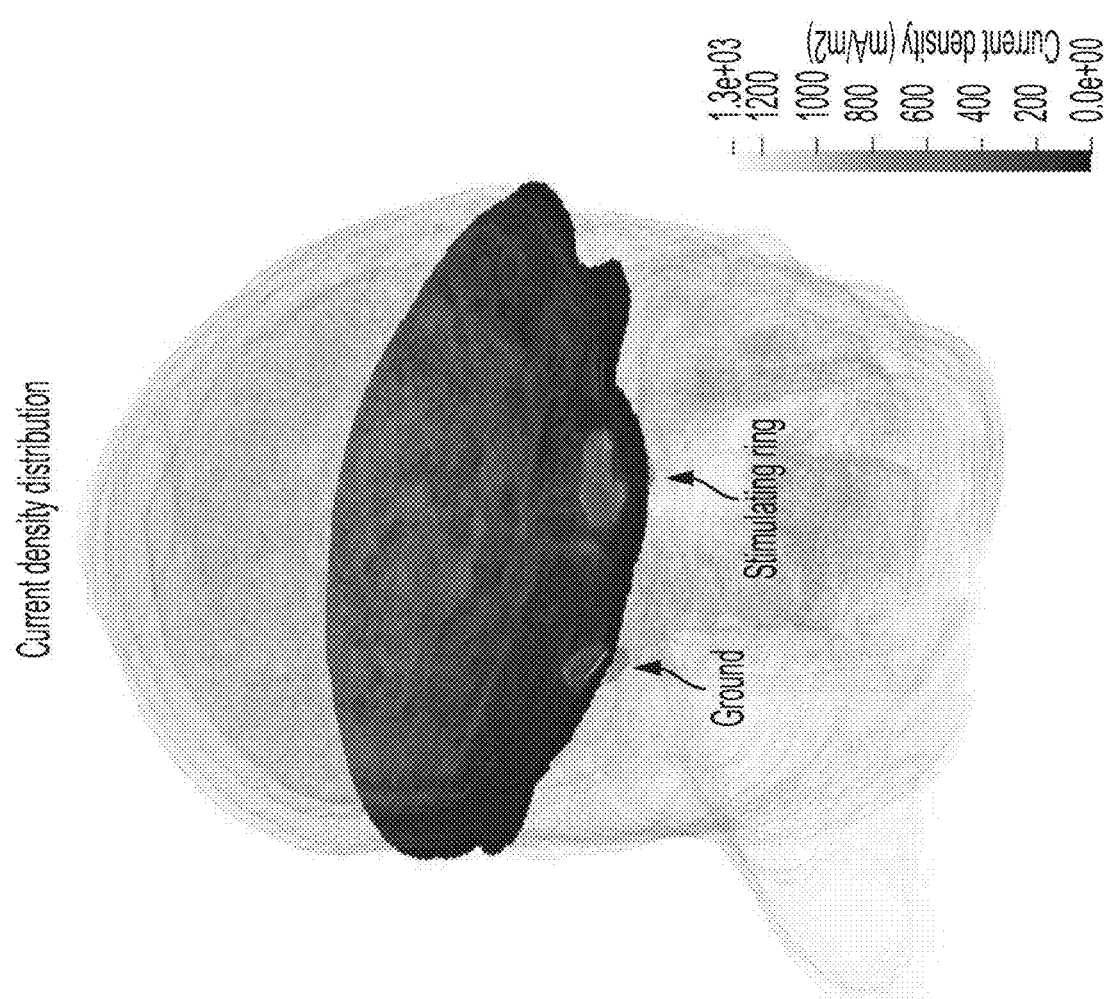
FIG. 14B illustrates a slice of the current density distribution in the embodiments of FIGS. 13A-B according to an aspect of the present disclosure.

FIG. 14A illustrates a slice of the voltage distribution in the embodiments of FIGS. 13A-B. FIG. 14B illustrates a slice of the current density (a maxima current density) distribution in the embodiments of FIGS. 13A-B. A system with a small return electrode may confine the current flow to the eye and the electrical stimulation may target the retinal neurons and nerves.

Figure 15A:
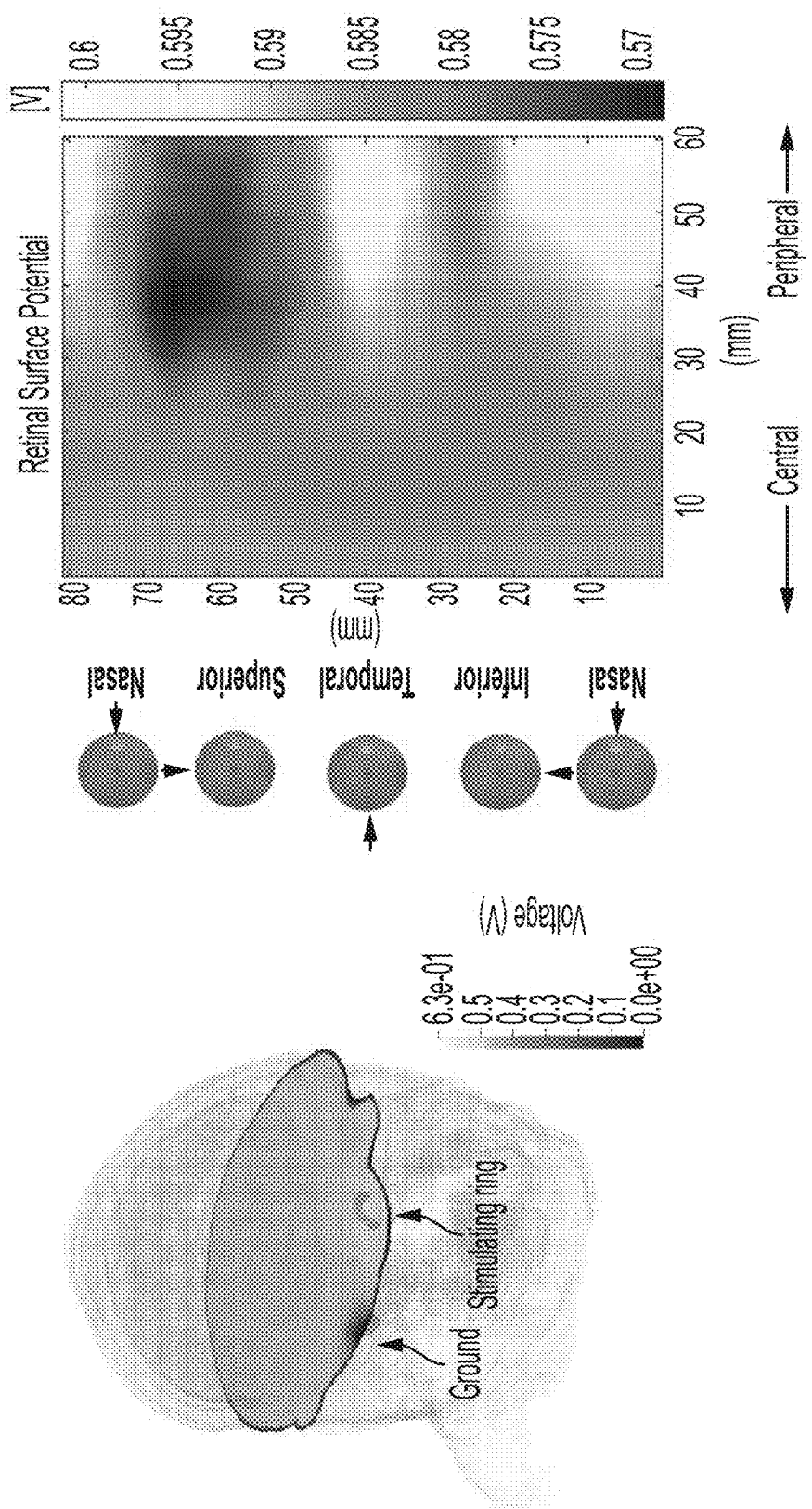
FIGS. 15A illustrates the retinal surface potential in the embodiments of FIGS. 13A-B according to an aspect of the present disclosure.
Figure 15B:
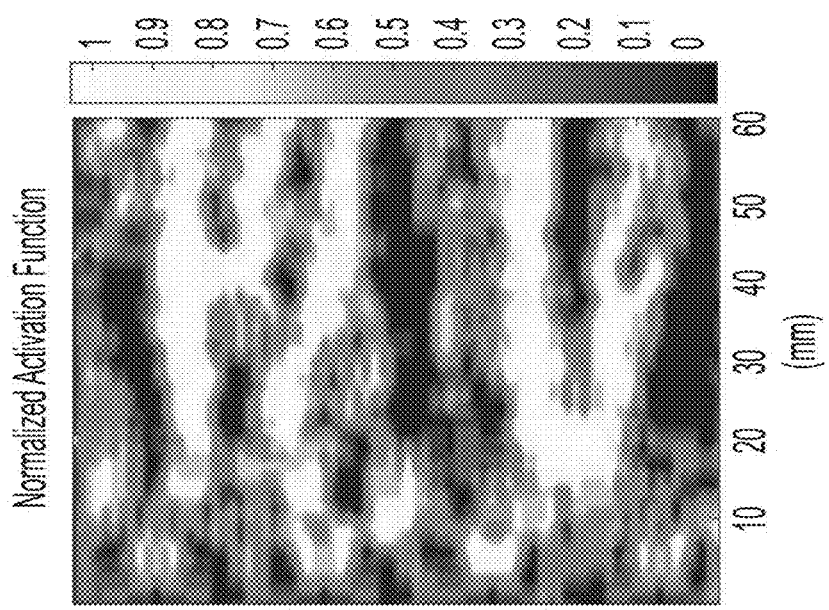
FIG. 15B illustrates the activation function in the embodiments of FIGS. 13A-B according to an aspect of the present disclosure.

FIGS. 15A illustrates the retinal surface potential in the embodiments of FIGS. 13A-B. The regions with the highest probability of retinal neurons activation may be described with the normalized activation function. The illustrated embodiments of FIG. 13A-B may generate a uniform and consistent neuronal activation area at both central and peripheral retina. FIG. 15B illustrates the activation function in the embodiments of FIGS. 13A-B. Embodiments described herein supports the efficacy of the designed electrical stimulation strategy to slow down relentless and aggressive retinal degeneration in clinical studies.

Figure 16A:
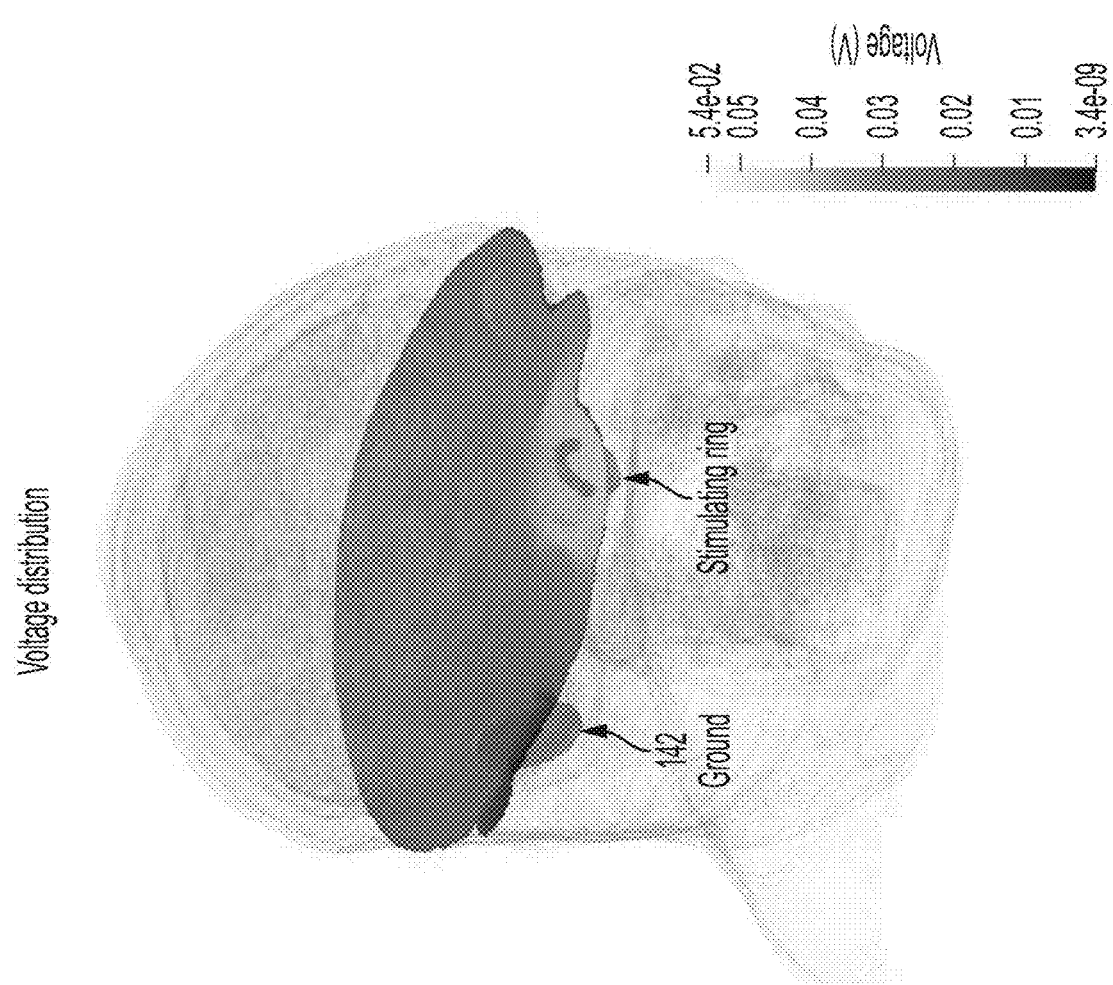
FIG. 16A illustrates a slice of the voltage distribution according to an aspect of the present disclosure.
Figure 16B:
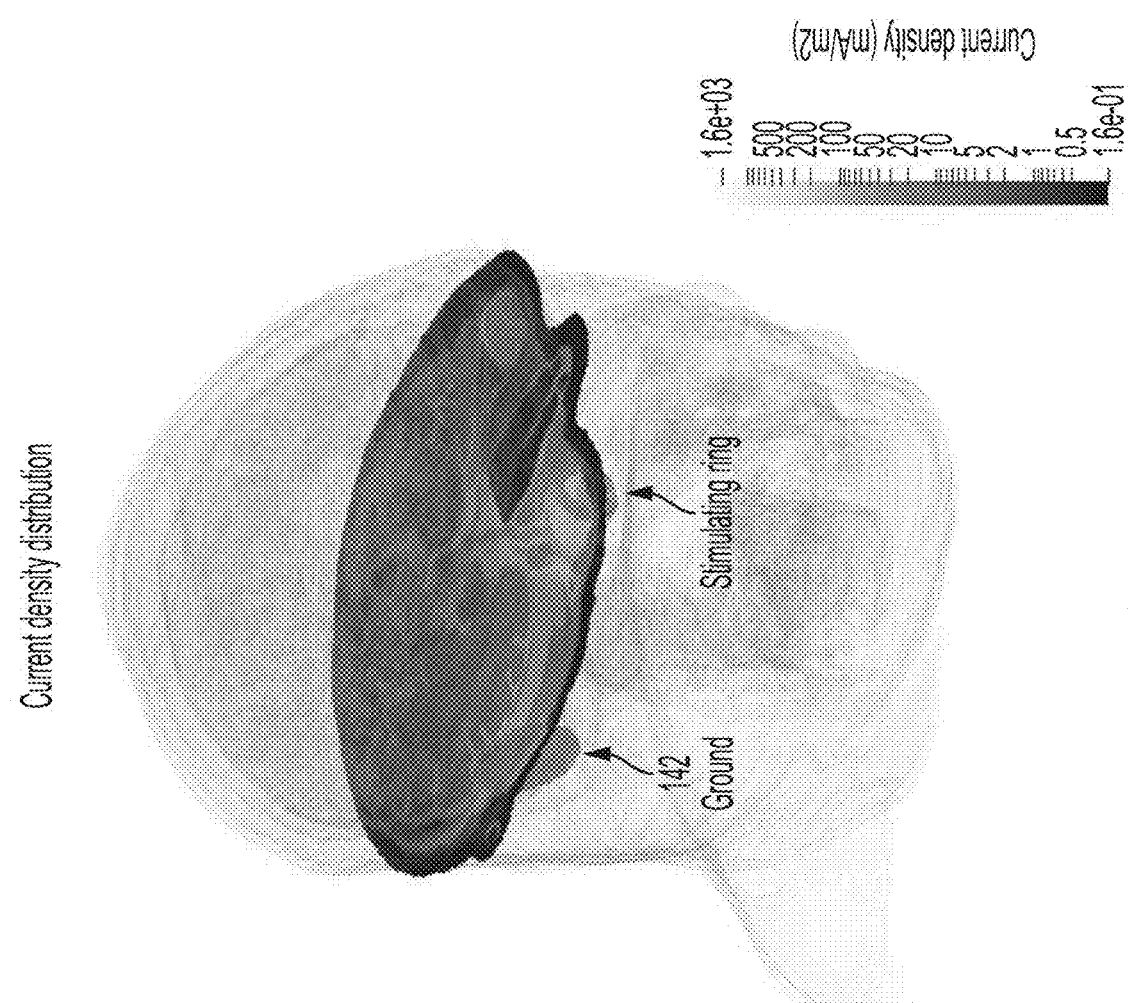
FIG. 16B illustrates a slice of the current density distribution according to an aspect of the present disclosure.

FIG. 16A illustrates a slice of the voltage distribution and FIG. 16B illustrates a slice of the current density distribution of a system having a larger surface area of the ground electrode 142. The embodiment described herein has shown that a large return electrode may lead to a low resistance path to the ground, thereby increasing the current flow to the retina. Small return electrodes enhance the current density magnitude near the electrode. Using the large return electrode further reduces the current density in the temporal region and allows for safe application of transcorneal electrical stimulation and reduce the discomfort of patients during the application of TES. The embodiment described herein allows to better target the outer retinal neurons which are damaged at the early stages of retinal degeneration, thereby may be used for therapeutic treatments. Various electrode geometry, shapes, and sizes may be utilized to control induced electric fields and currents and therefore the activation of neurons including that of the retina.

Figure 17A:
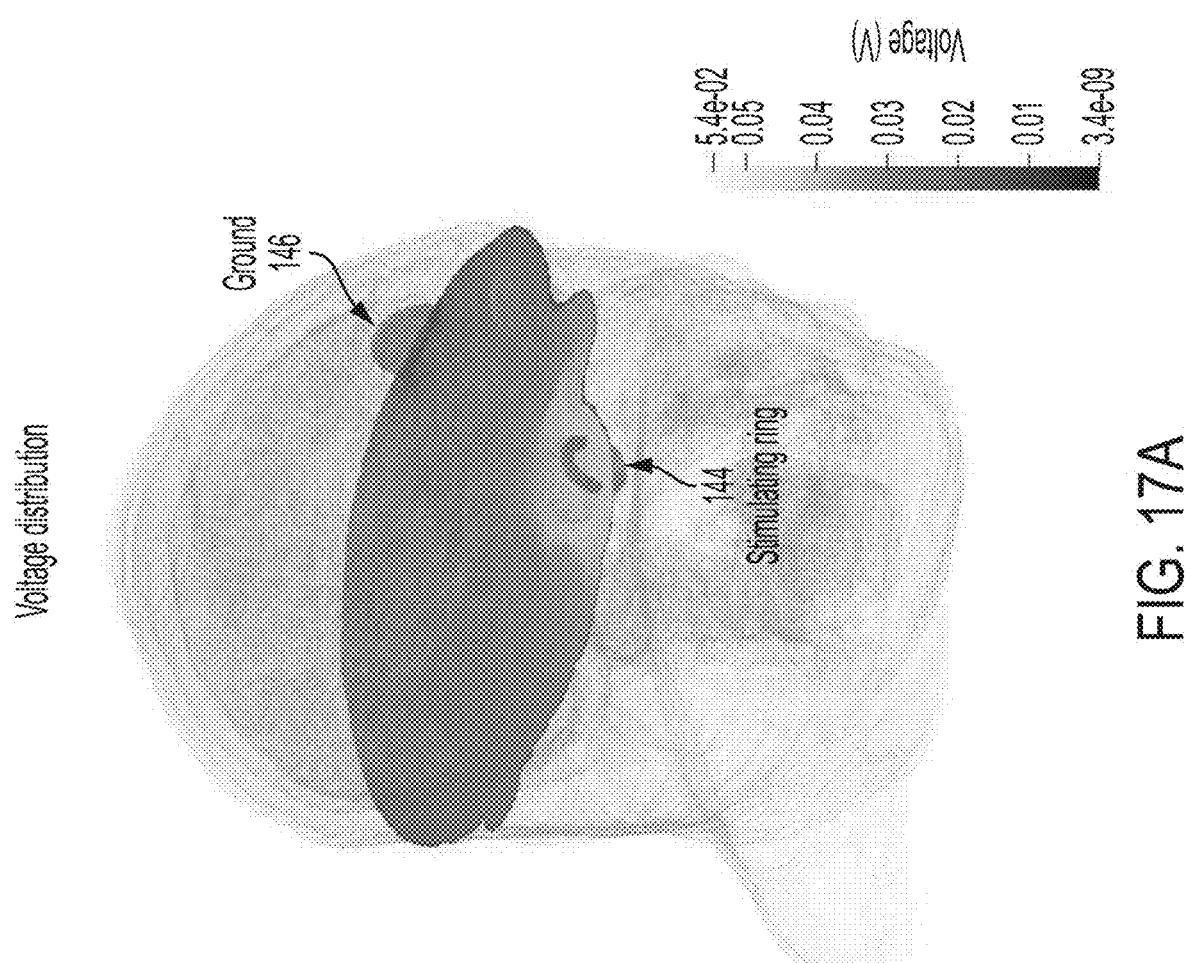
FIG. 17A illustrates a slice of the voltage distribution with a ground electrode on a temporal site of a non-stimulated eye according to an aspect of the present disclosure.
Figure 17B:
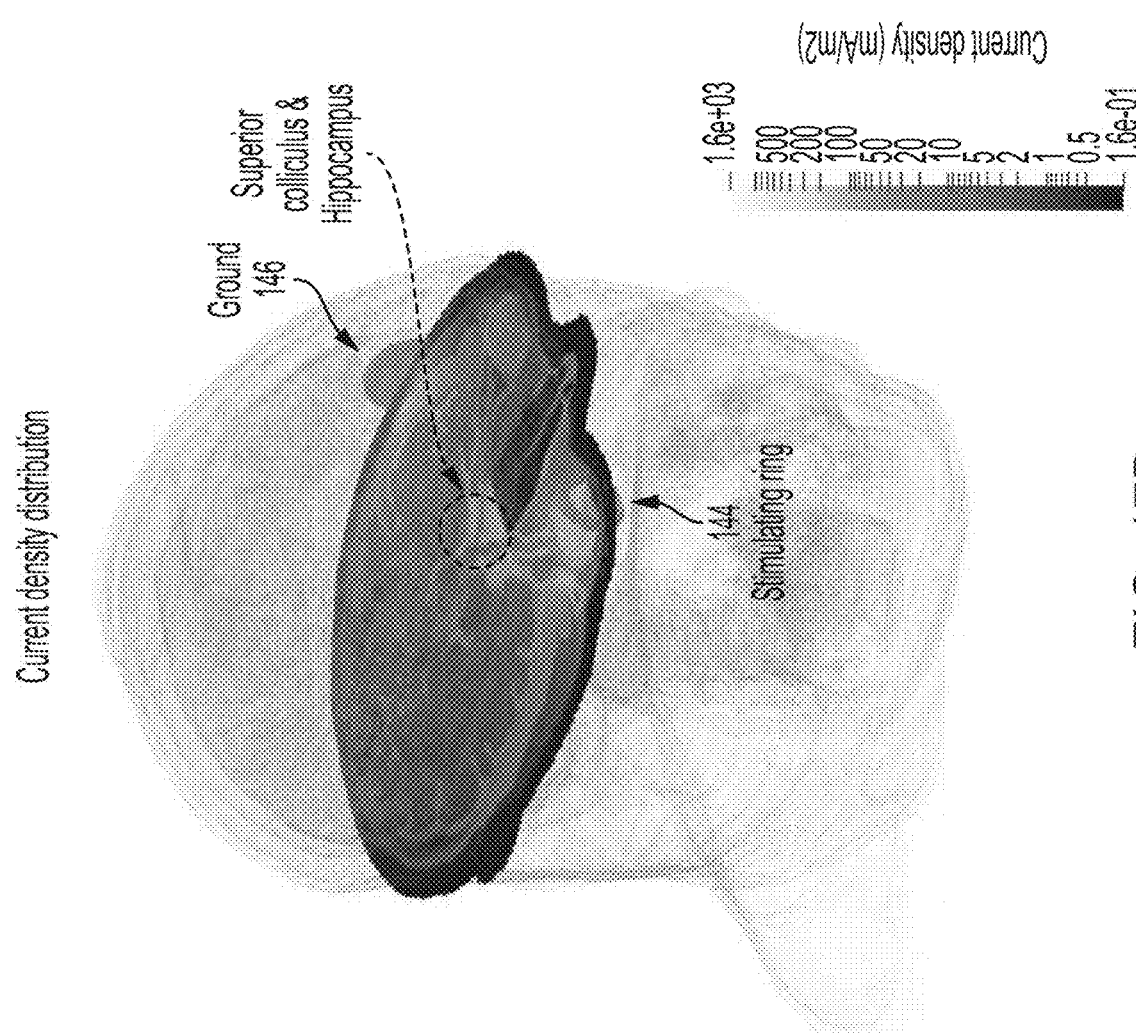
FIG. 17B illustrate a slice of the current density distributions with a ground electrode on a temporal site of a non-stimulated eye according to an aspect of the present disclosure.

FIG. 17A illustrates a slice of the voltage distribution due to the stimulation of a ring electrode 144 with a ground electrode 146 on a temporal site of a non-stimulated eye. FIG. 17B is the computational result of the current density flow in the eye and the brain. Changing the position of the return electrode may alter the direction of current flow in the human tissue. The generation of electric fields along the optic nerve has been shown to result in retinal ganglion axonal growth and therefore regeneration of the damaged optic nerve. The embodiment shown in FIG. 17B may be utilized to enhance the current flow throughout the optic nerve for diseases such as Glaucoma. The maxima current density is in the eye including the retina and a substantial amount of current enters to the optic nerve and optic chiasm. FIG. 17B further illustrates that with the proper adjustment of the large return electrode the current density in the superior colliculus may be augmented, providing the opportunity to preserve neurons sending visual signals to the brain and reinnervation. Enhanced induced current density in the central region of the brain further opens the door for other regions within the central nervous system (CNS) such as increased electrical gradients at the level of the hippocampal neurons. This implies that this type of electrical stimulation may be utilized for restoration of vision in patients with the damaged optic nerve suffering from retinal diseases such as Glaucoma and may be further extended to other area therapeutic applications secondary to other neurodegenerative diseases of the CNS.

Figure 18A:
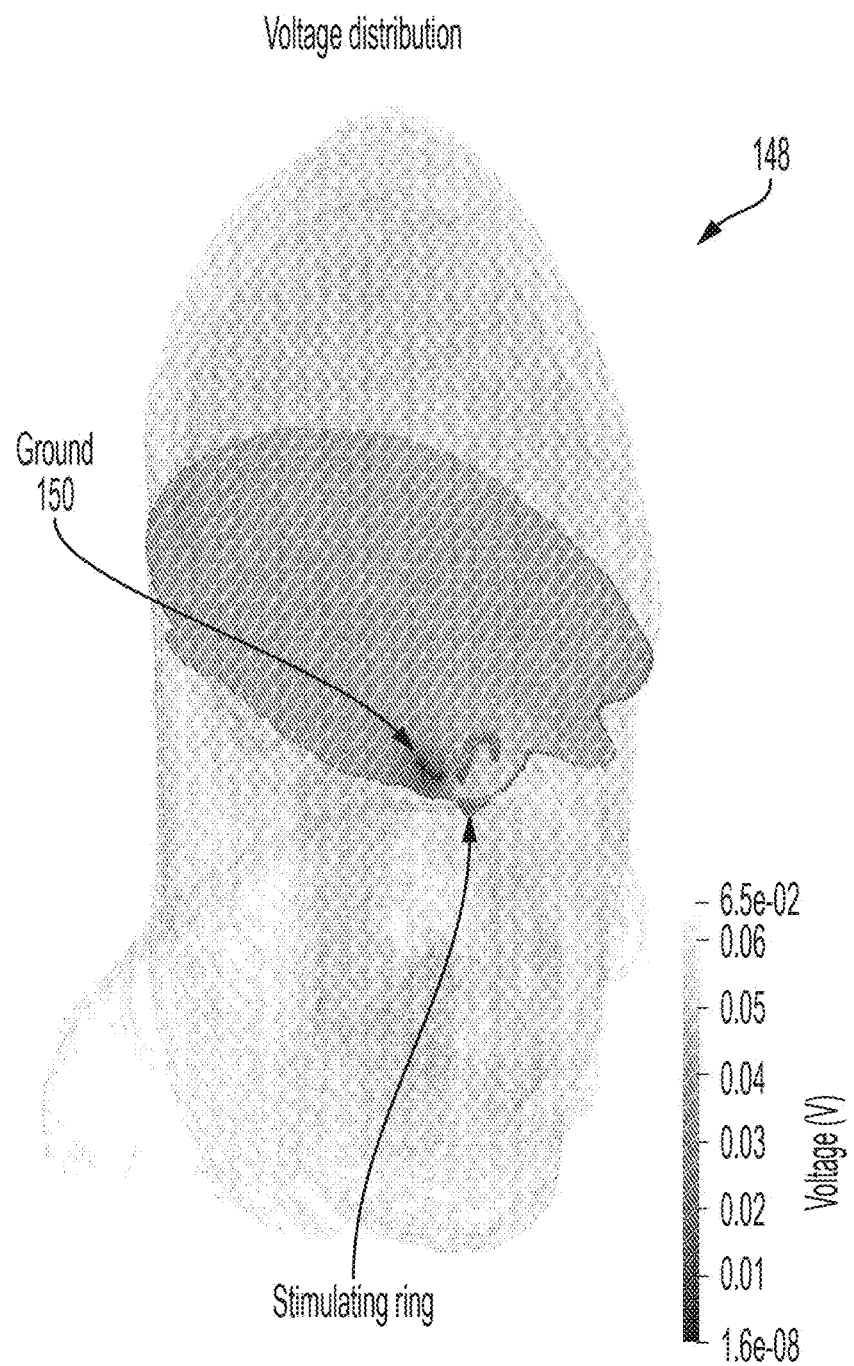
FIG. 18A illustrates a slice of the voltage distribution for a wired E-lens system with a ground electrode positioned inferiorly inside an eyelid according to an aspect of the present disclosure.
Figure 18B:
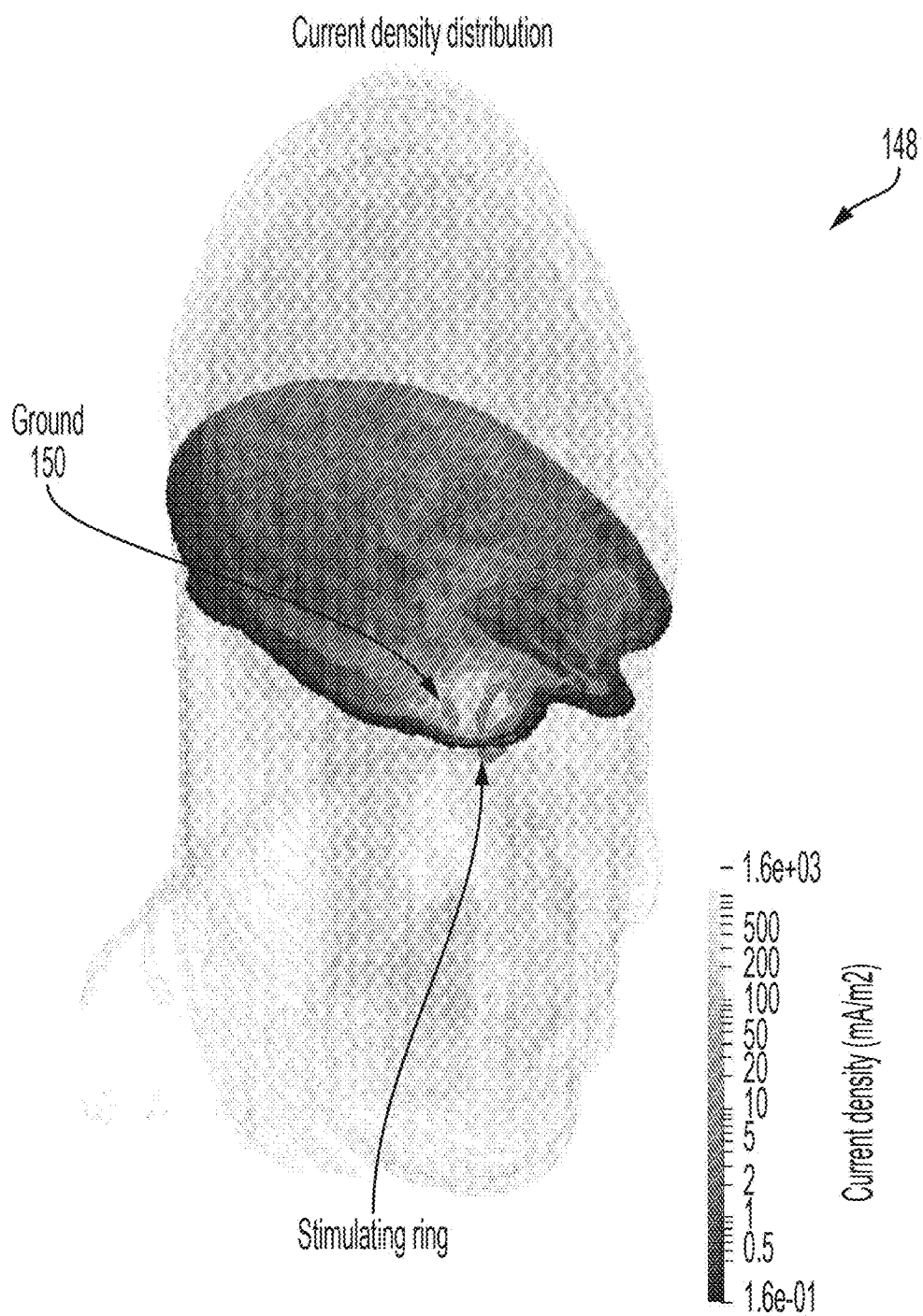
FIG. 18B illustrates a slice of the current density distribution for the system of FIG. 18A according to an aspect of the present disclosure.

FIG. 18A is illustrates a slice of the voltage distribution for a wired E-lens system 148 with a ground electrode 150 positioned inferiorly inside an eyelid. FIG. 18B illustrates a slice of the current density distribution for the system 148 of FIG. 18A.

Figure 19A:
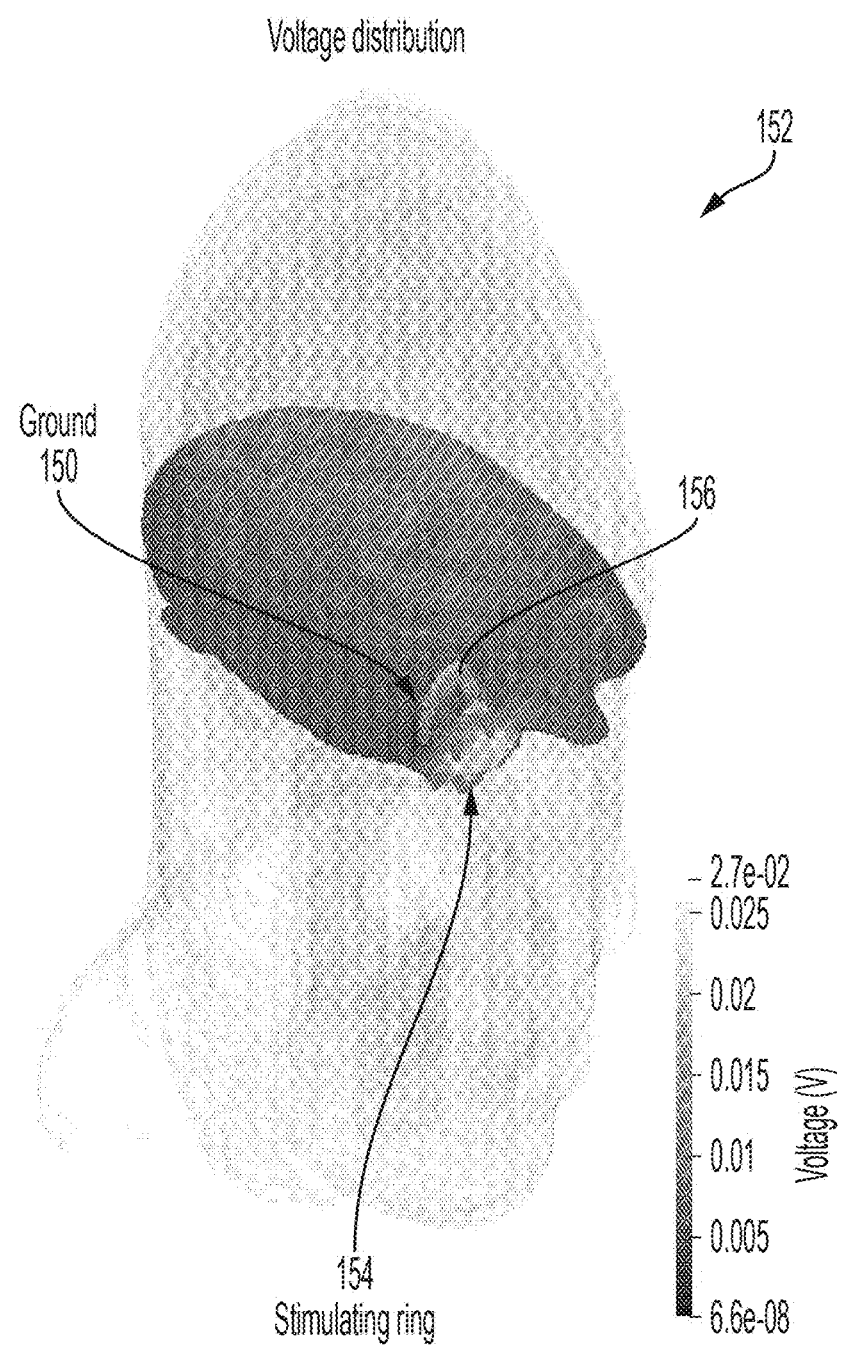
FIG. 19A illustrates a slice of the voltage distribution for a wired E-lens system with stimulating and return ring electrodes on the eye according to an aspect of the present disclosure.
Figure 19B:
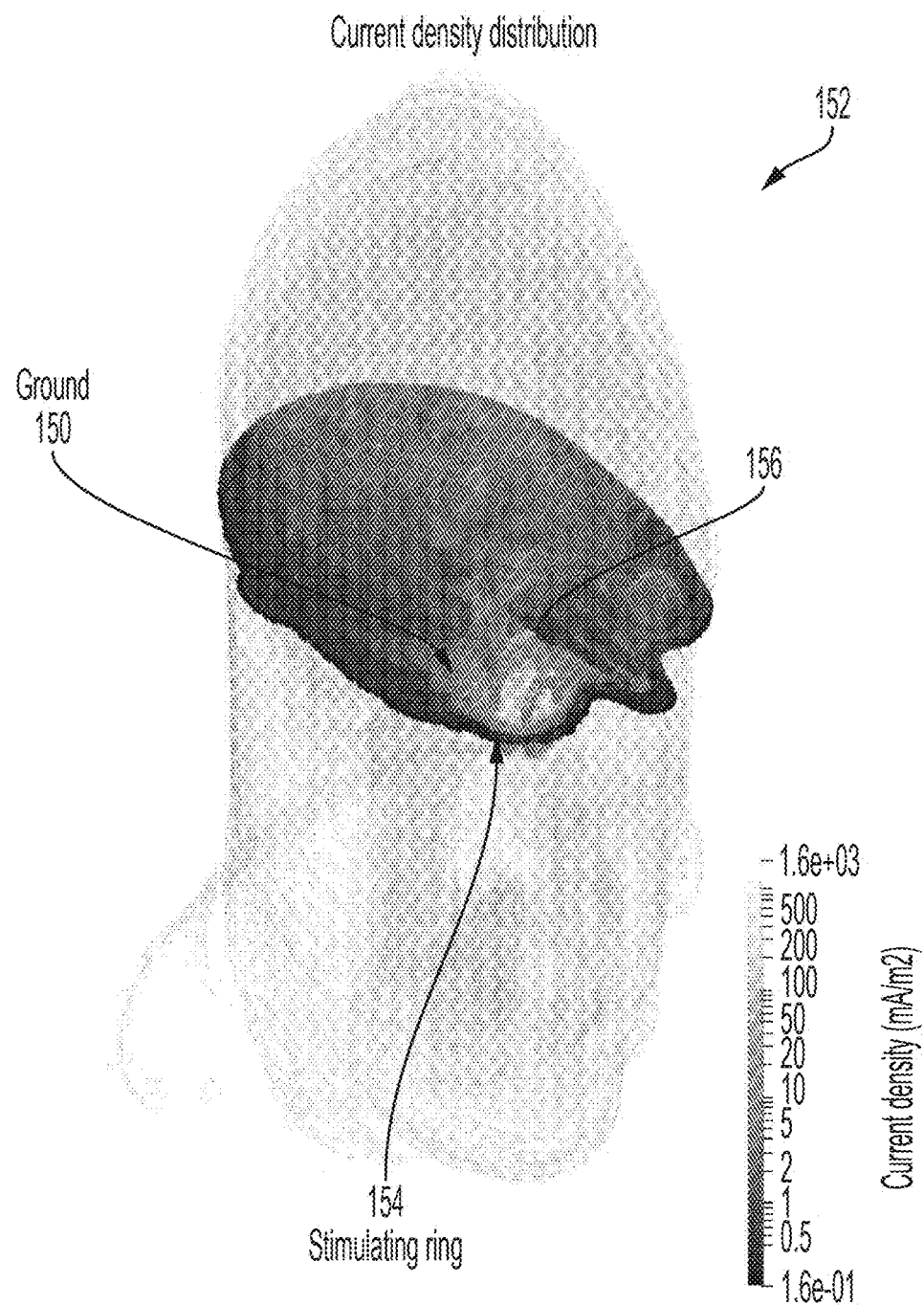
FIG. 19B illustrates a slice of the current density distribution for the system of FIG. 19A according to an aspect of the present disclosure.

FIG. 19A illustrates a slice of the voltage distribution for a wired E-lens system 152 with stimulating ring 154 and return ring 156 electrodes on the eye. FIG. 19B illustrates a slice of the current density distribution for the system 152 of FIG. 19A. The return ring 156 electrode may be placed on the eye posterior to the stimulating ring 154 electrode. The embodiment described herein may focalize the current density distribution into the eye and enable focal activation of different retinal regions by proper selections of stimulus waveforms.

Figure 20:
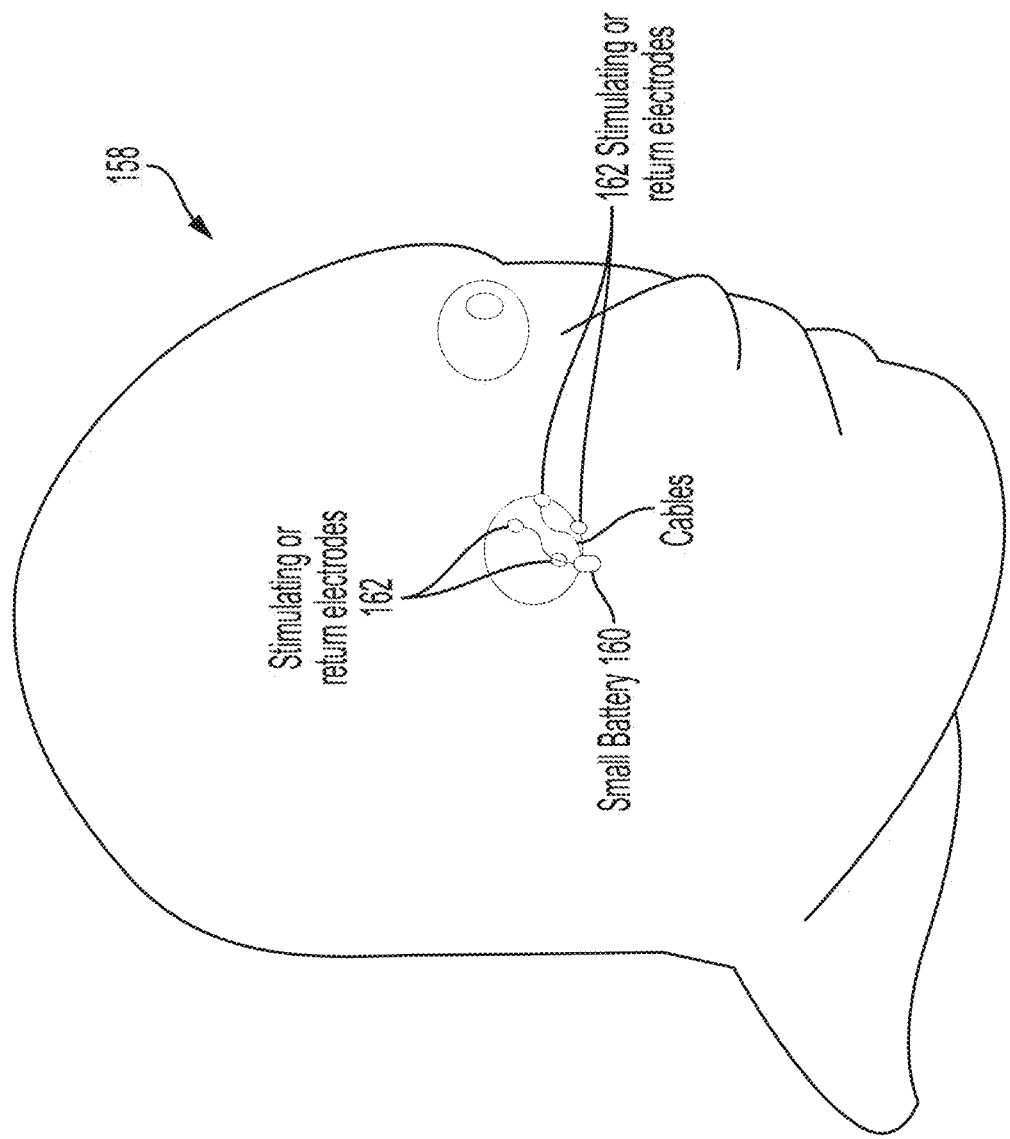
FIG. 20 illustrates a wired E-lens system with a powered battery positioned inferiorly inside an eyelid according to an aspect of the present disclosure.

FIG. 20 illustrates a wired E-lens system 158 with a powered battery 160 positioned inferiorly inside an eyelid and electrodes 162 on an eye. The battery 160 may be placed on the eye inferiorly inside the eyelids. Both the stimulating and the return electrode of the electrodes 162 may be connected by cables to the battery 160 to provide the power supply for electrical stimulation.

FIG. 21 illustrates a wireless E-lens system 164. The embodiments described herein may be implemented in a contact lens 166. An external coil 168 may transfer power wirelessly to an internal receiver coil 170. The system 164 may have resonating capacitors 172, inductors, and diodes for maximum power delivery and efficiency as well as generating a desired stimulus waveform. The system 164 may include the stimulating and return electrodes 174 placed on the eye.

Figures 22A, 22B:
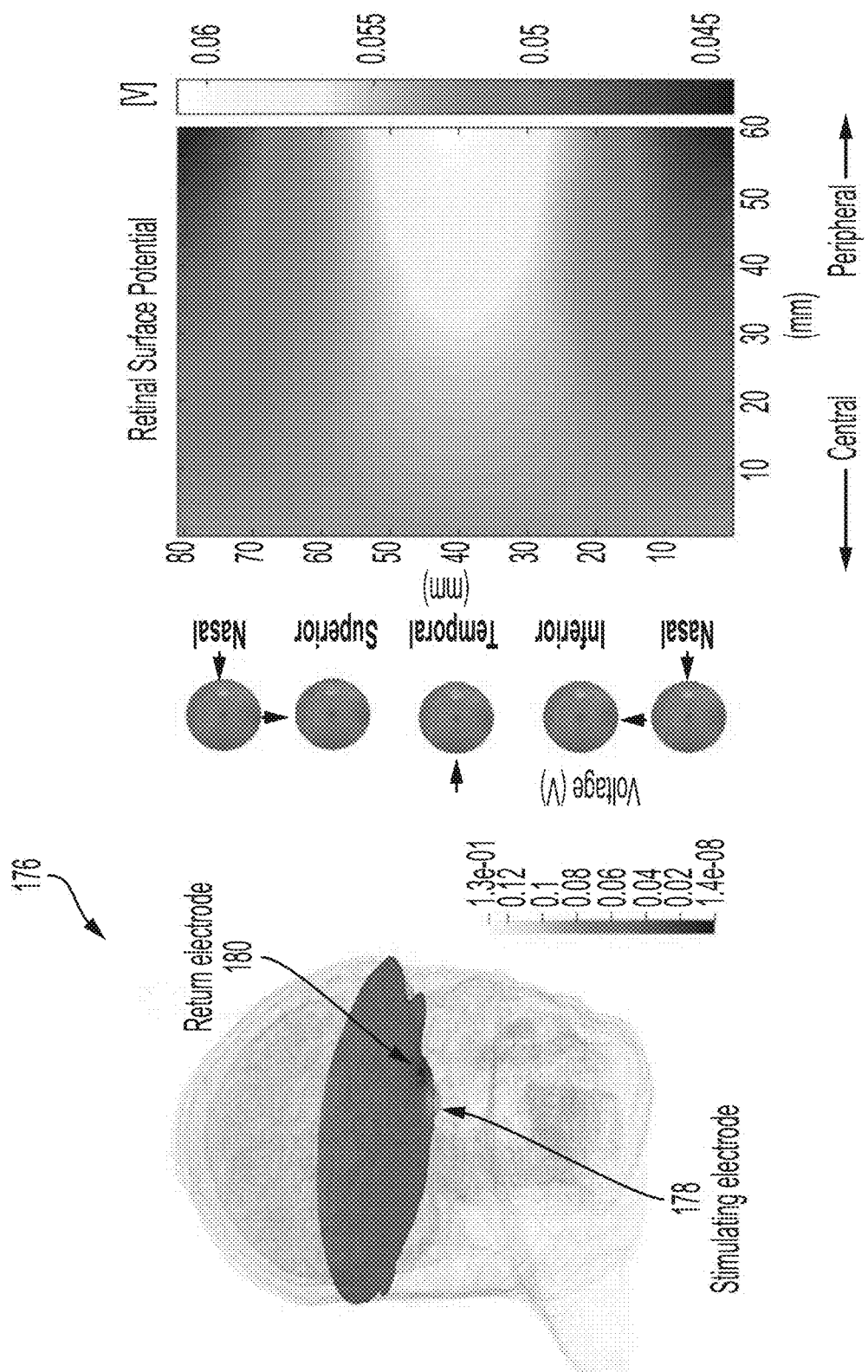
FIG. 22A illustrates an embodiment of an E-lens system according to an aspect of the present disclosure.
FIG. 22B illustrates the retinal surface potential in the embodiment of FIG. 22A according to an aspect of the present disclosure.
Figure 22C:
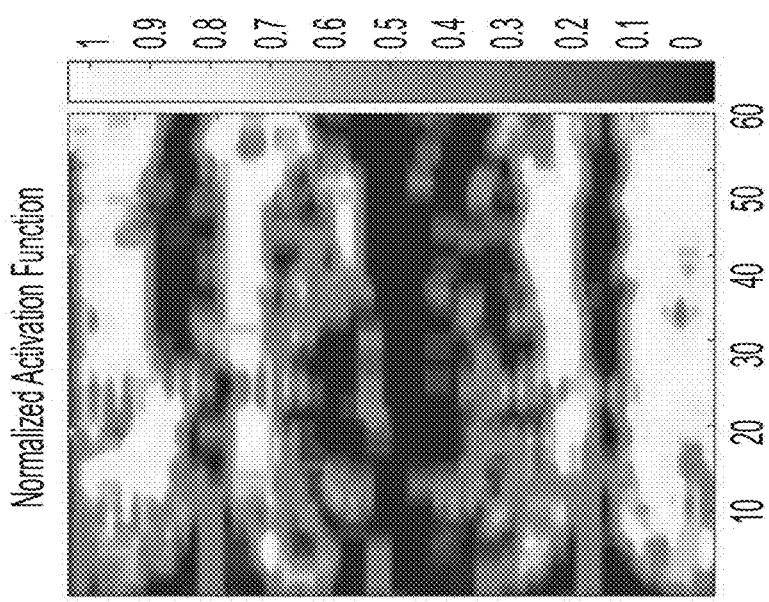
FIG. 22C illustrates the normalized activation function in the embodiment of FIG. 22A according to an aspect of the present disclosure.

FIG. 22A illustrates an embodiment of an E-lens system 176. Stimulation and return electrodes 178, 180 may be placed close to the temporal and nasal areas, respectively. The positions of the electrodes 178, 180 on the eye may be arranged such that the activation threshold area is maximized and achieve uniform induced electric fields in the retina including the central to peripheral regions. The electric potentials on the surface of the retina are mapped into a 2D plane and the activation function principle is utilized to determinate regions where the retinal neurons may be activated. FIG. 22B illustrates the retinal surface potential distribution in the embodiment of FIG. 22A. The retinal surface potential distribution may be extracted from the human head model and projected into a 2D map. FIG. 22C illustrates the normalized activation function in the embodiment of FIG. 22A. The normalized activation function describes the most probable activation region of neurons.

Figures 23A, 23B:
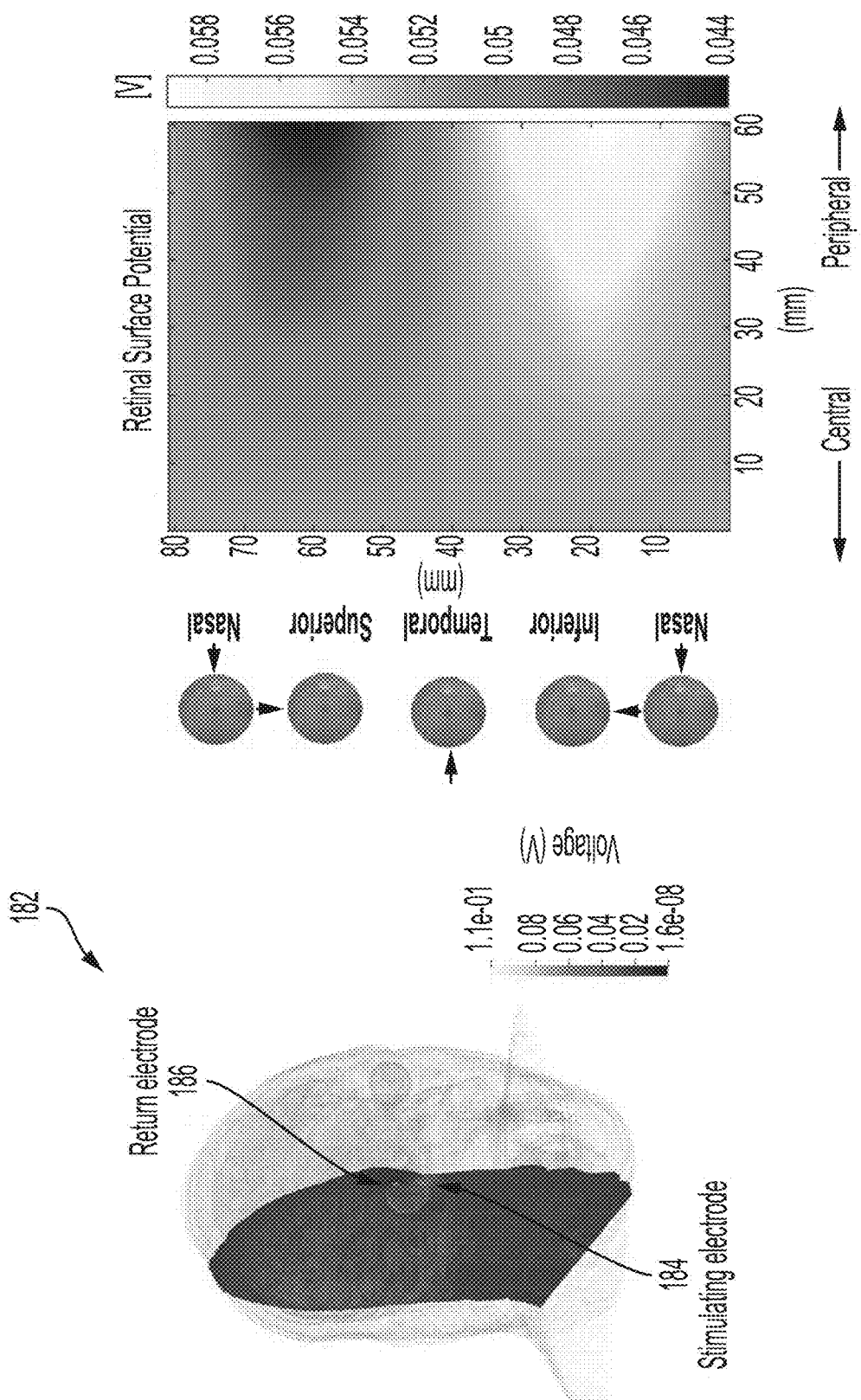
FIGS. 23A illustrates an embodiment of an E-lens system according to an aspect of the present disclosure.
FIG. 23B illustrates the retinal surface potential in the embodiment of FIG. 23A according to an aspect of the present disclosure.
Figure 23C:
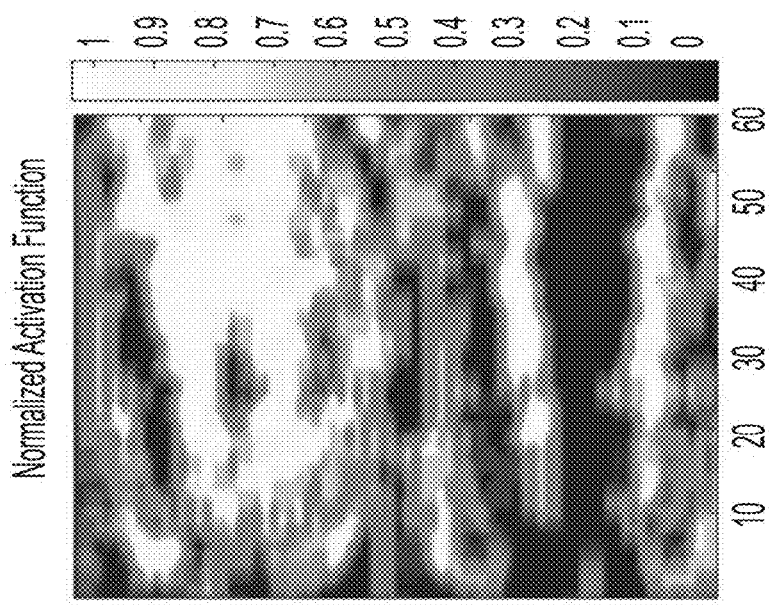
FIG. 23C illustrates the normalized activation function in the embodiment of FIG. 23A according to an aspect of the present disclosure.

FIGS. 23A illustrates an embodiment of an E-lens system 182 with an alternative stimulating ring 184 and return electrode 186 placement. The E-lens system 182 may be a wireless system. The system 182 may alter the direction of the current flow and the induced electric fields magnitude in the retinal region. FIG. 23B illustrates the retinal surface potential in the embodiment of FIG. 23A. FIG. 23C illustrates the normalized activation function on the surface of the retina in the embodiment of FIG. 23A. According to the activating function principle, the total current flux flowing in and out of the cells must be equal, leading to equal strength of the depolarization and hyperpolarization of neurons. Therefore, uniform activation of neurons using one specific electrode placement and configuration is challenging. The combination of the electrode placements with exclusive ocular electrical stimulation using the wireless E-lens system 182 may generate almost a consistent activation of retinal neurons in different regions.

Figures 24A, 24B:
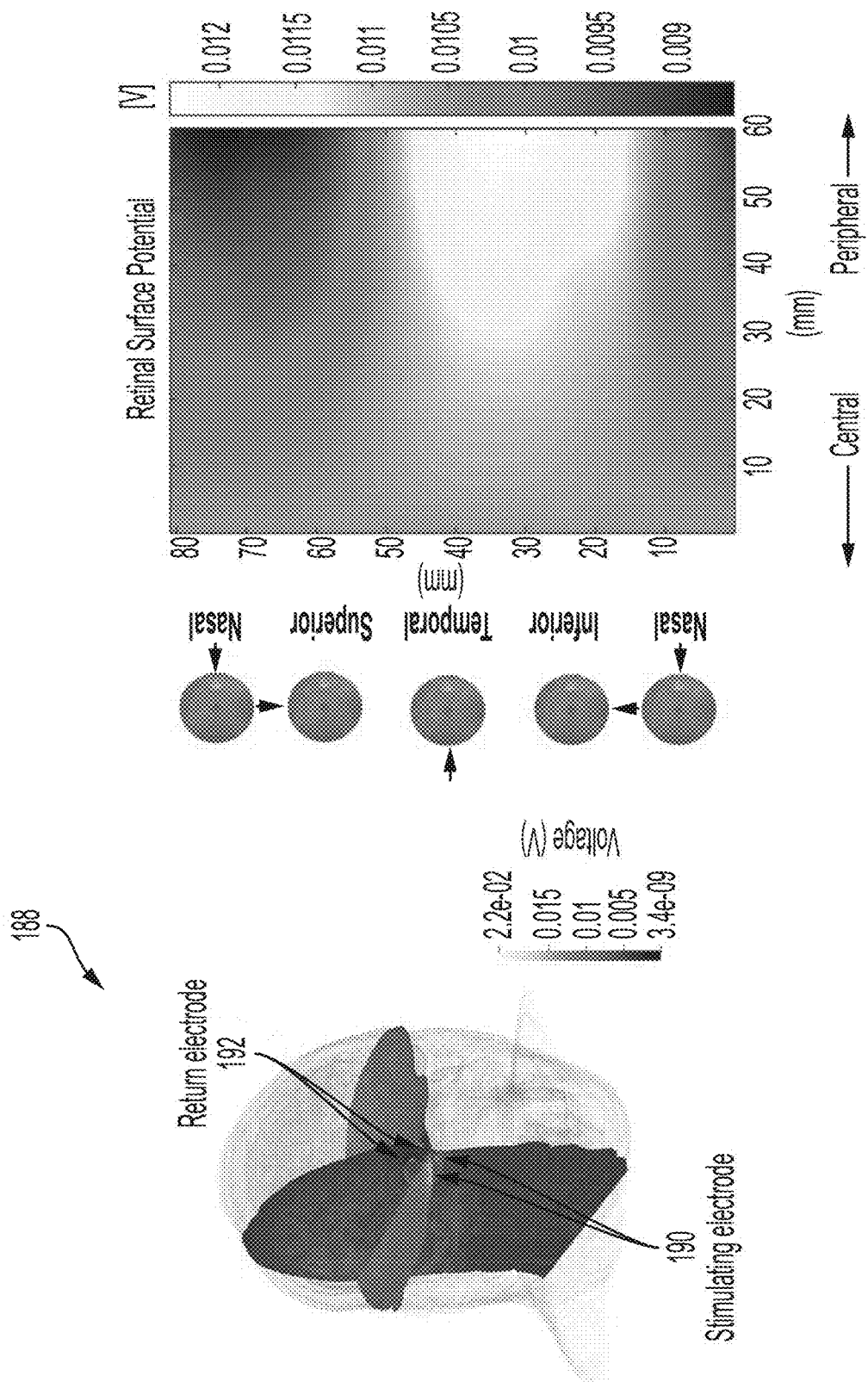
FIGS. 24A illustrates an embodiment of an E-lens system according to an aspect of the present disclosure.
FIG. 24B illustrates the retinal surface potential in the embodiment of FIG. 24A according to an aspect of the present disclosure.
Figure 24C:
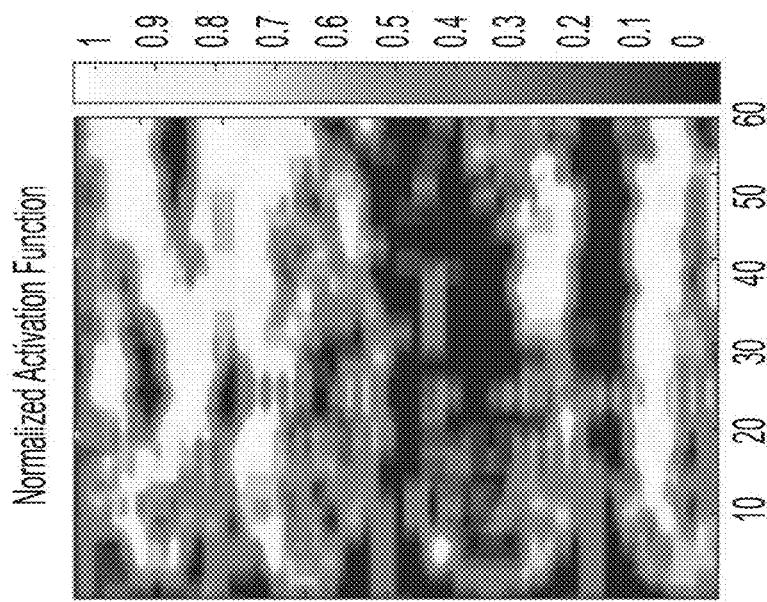
FIG. 24C illustrates the normalized activation function in the embodiment of FIG. 24A according to an aspect of the present disclosure.

FIG. 24A is another embodiment of an E-lens system 188 having two combinations of stimulating and return electrodes 190, 192 illustrating the slices of resulting electrical potential distribution. FIG. 24B illustrates the retinal surface potential in the embodiment of FIG. 24A. FIG. 24C illustrates the normalized activation function in the embodiment of FIG. 24A. The illustrated retinal surface electric potential and activation regions in FIGS. 23B-23C indicate that the induced electric fields and current flow may be altered by selections of stimulation and return electrodes 190, 192. Accordingly, with a proper selection of electrodes placed on the eye and simulations or exclusive transcranial electrical stimulation, a great coverage of neuronal activation region may be achieved, leading to better and consistent therapeutic effects. Various electrode geometries, configurations, and placements may be utilized to uniformly induce electric fields in different regions and therefore target cells of interest.

Figure 25A:
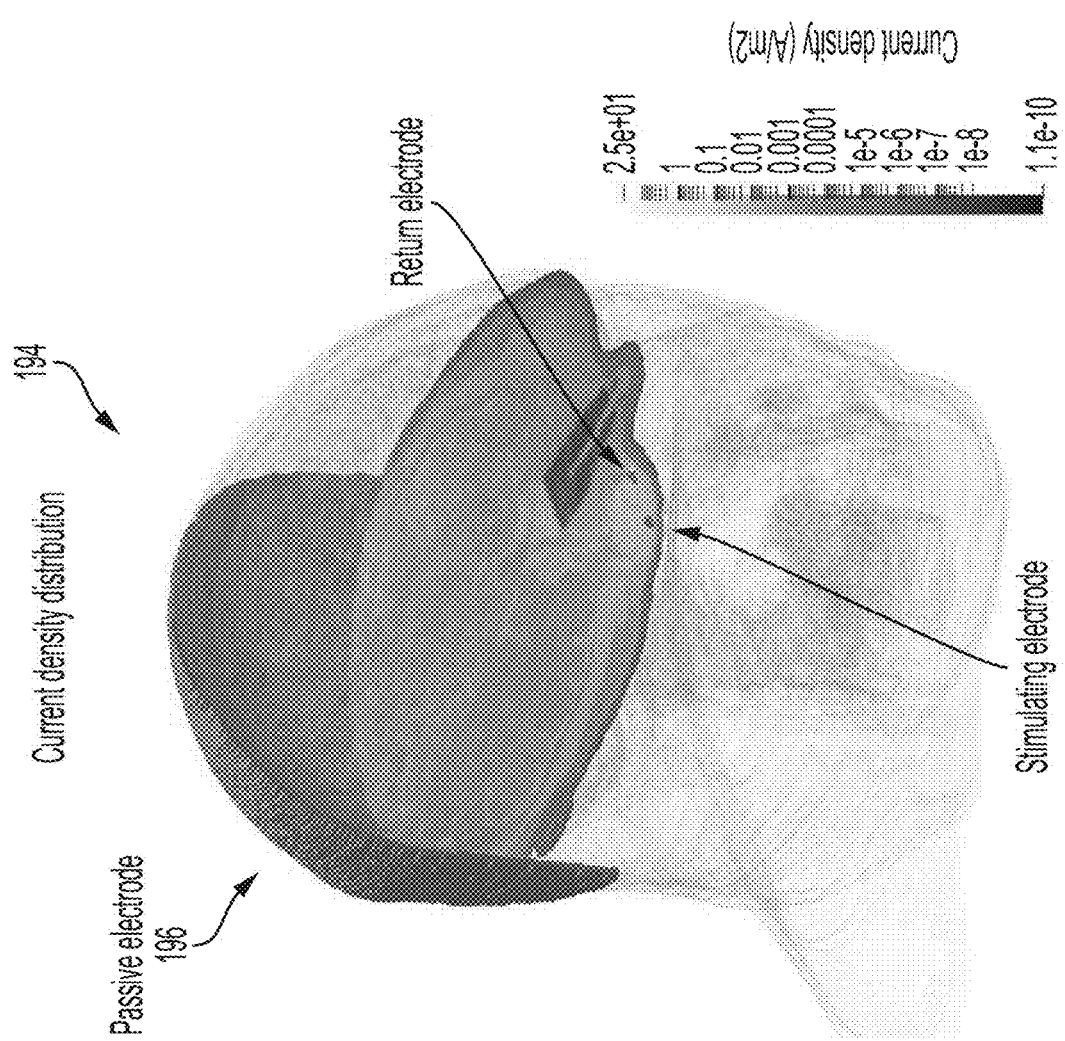
FIG. 25A illustrates a simulation of an E-lens system with a passive electrode according to an aspect of the present disclosure.
Figure 25B:
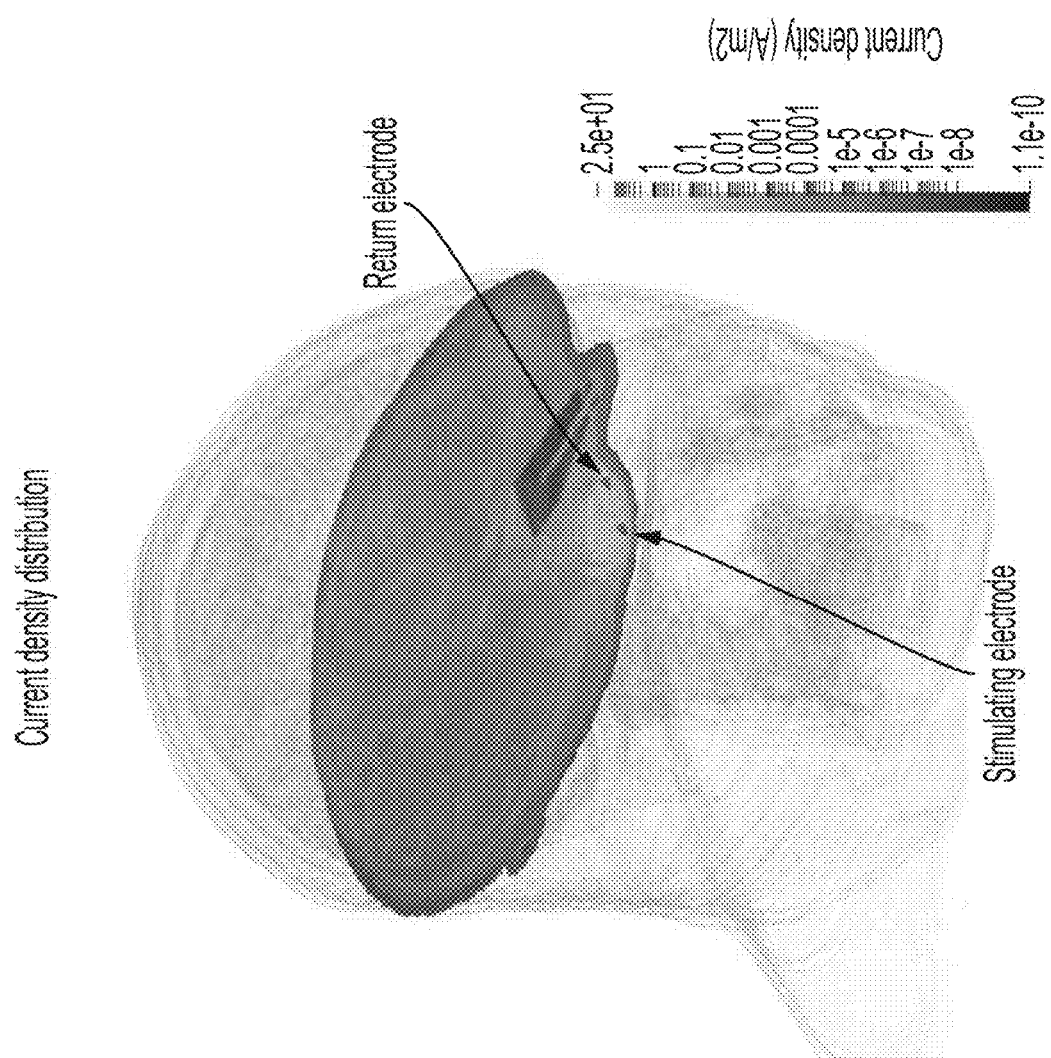
FIG. 25B illustrates a simulation of an E-lens system without a passive electrode according to an aspect of the present disclosure.

FIGS. 25A-25B illustrate a simulation of an E-lens system 194 with a passive electrode 196 comparing an accumulated current density magnitude with and without the addition of a passive electrode 196, which may have a large surface area and may be fastened on the back of the head. In the embodiment of FIG. 25A, the large passive electrode 196 placed on the back of the head may increase the total current density magnitude induced in tissues, nerves, and cells, including the brain and optic nerve compared to the embodiment of FIG. 25B. A passive electrode 196 may be beneficial to generate a low resistance path to different regions of the human body tissues and may increase the likelihood of targeting various neurons. Various shapes, geometries, and sizes of passive electrodes 196 may be utilized and fastened on different parts of the human head including the forehead and back of the head.

Figure 26A:
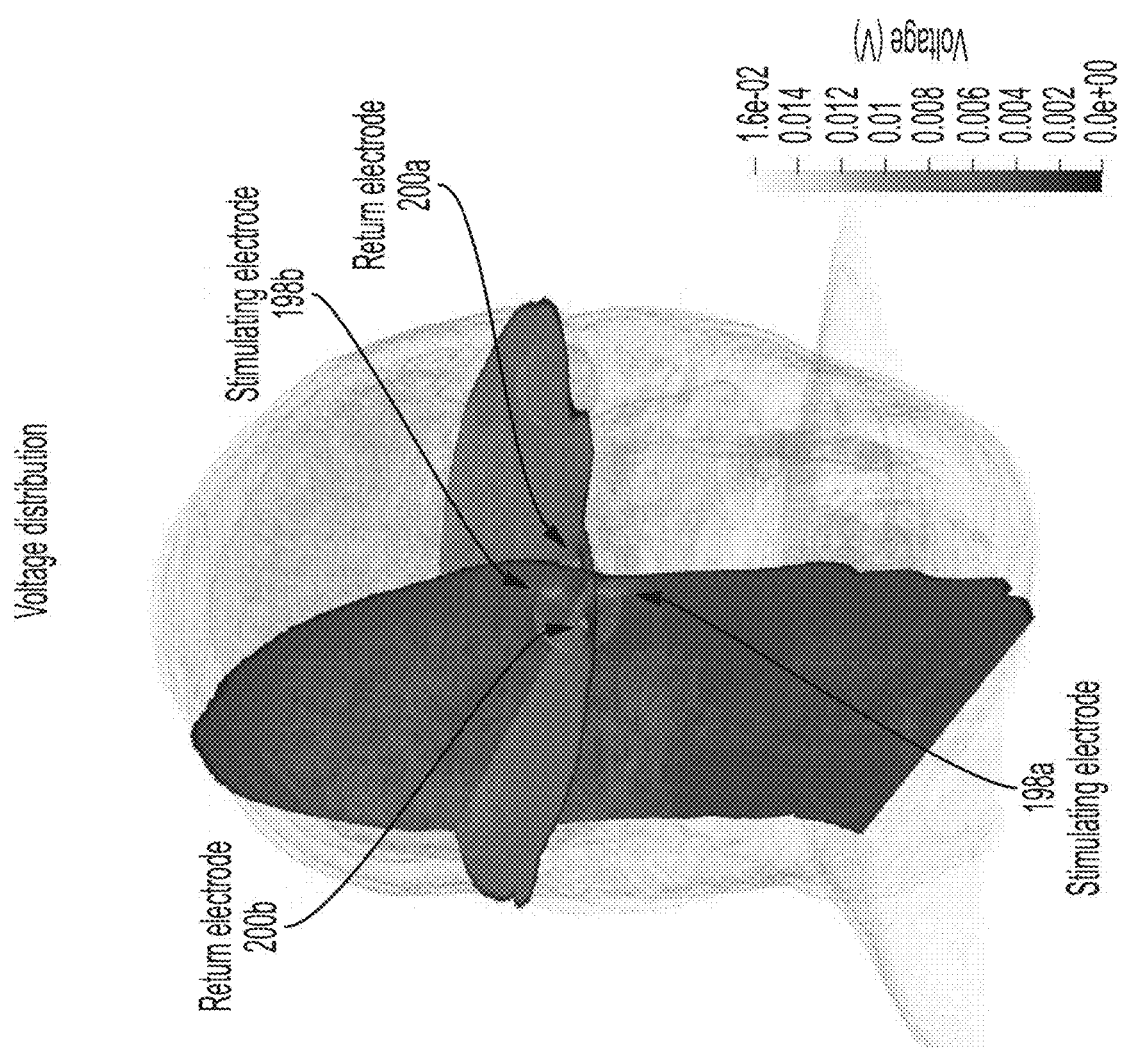
FIG. 26A illustrates a slice of the voltage distribution with adjacent stimulating and return electrodes according to an aspect of the present disclosure.
Figure 26B:
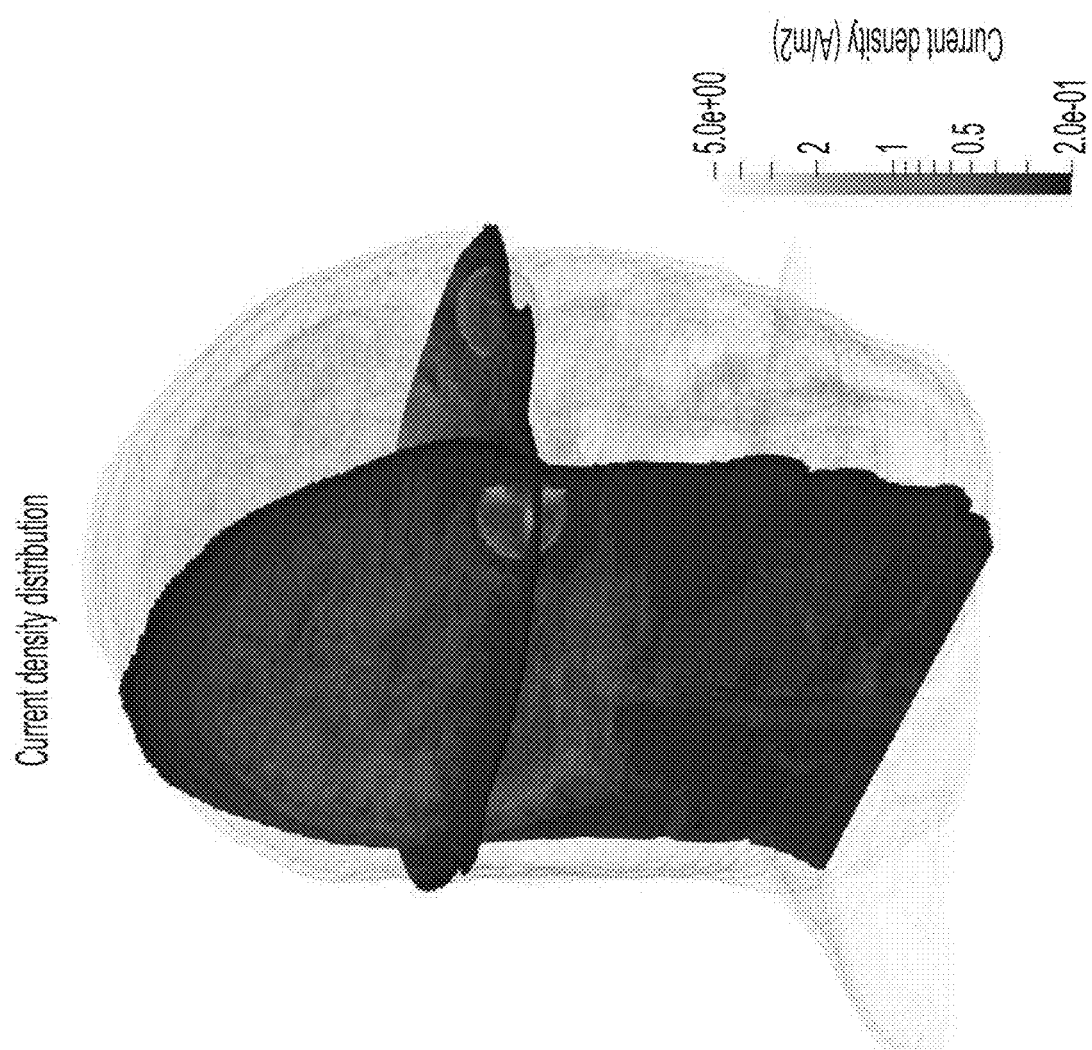
FIG. 26B illustrates a slice of the current density distribution with adjacent stimulating and return electrodes according to an aspect of the present disclosure.

FIG. 26A illustrates a slice of the voltage distribution with adjacent stimulating and return electrodes 198$a$-$b$, 200$a$-$b$. FIG. 26B illustrates a slice of the current density distribution with adjacent stimulating and return electrodes 198$a$-$b$, 200$a$-$b$. The embodiment shown in FIGS. 26A-26B illustrates the shortest path for the current flow may be generated between two adjacent stimulating and return electrodes 198$a$-$b$, 200$a$-$b$. This embodiment may be effective for activation of retinal neurons, tissues in the brain, and the optic nerve. The system design of this embodiment may be utilized for stimulation of corneal nerves as well as the lacrimal gland.

Figure 27:
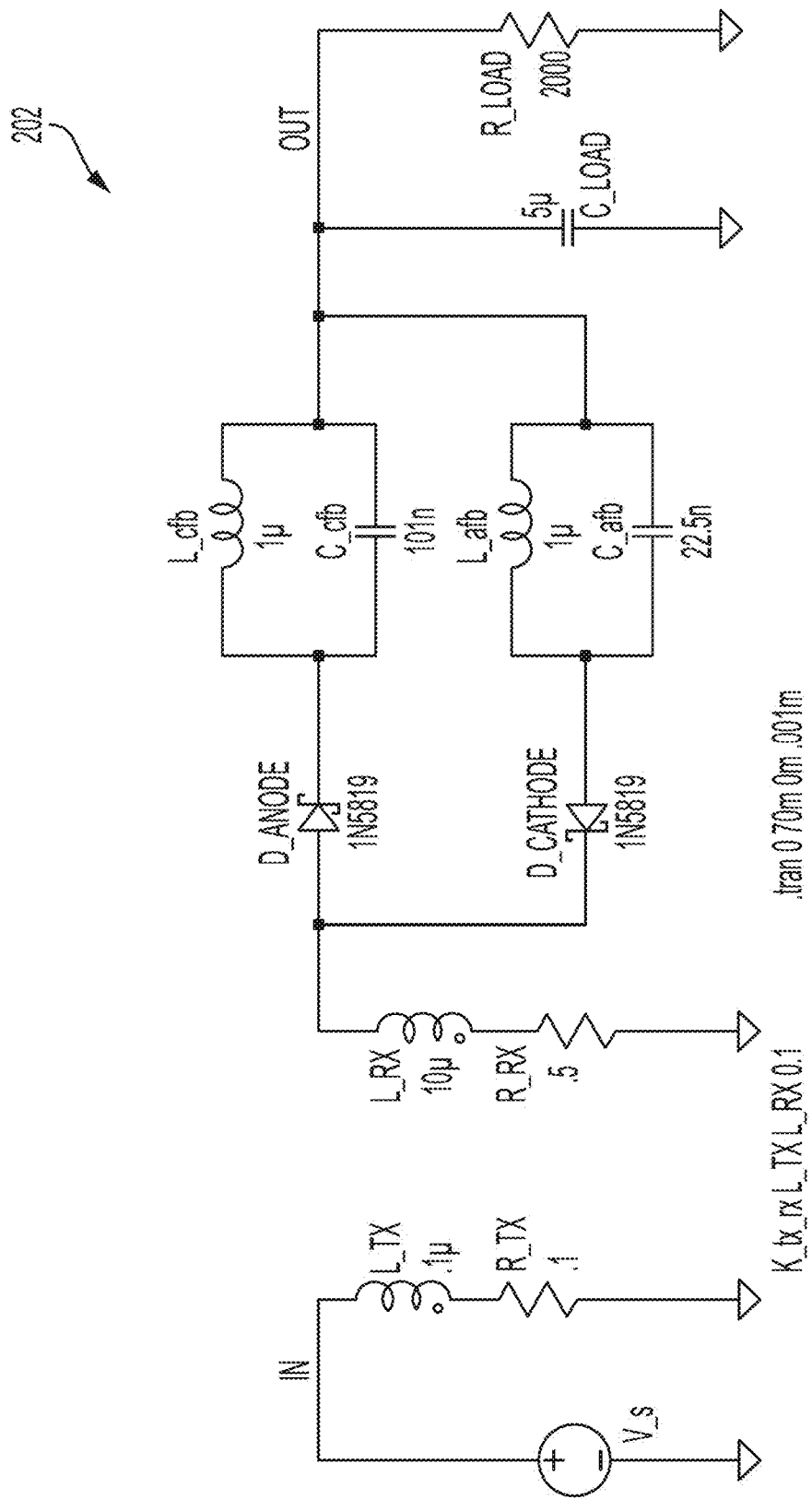
FIG. 27 illustrates a circuit schematic of a system that may provide wireless stimulation waveform to a single stimulating electrode according to an aspect of the present disclosure.

FIG. 27 illustrates a circuit 202 schematic of a system that may provide wireless stimulation waveform to a single stimulating electrode. The circuit 202 may efficiently deliver a charge balanced, symmetric, square biphasic pulse wirelessly to a wireless E-lens system. Inductors $L_{TX}$ and $L_{RX}$ are the inductances of the transmitter (TX) and receiver (RX) coils respectively. Resistors $R_{TX}$ and $R_{RX}$ are the internal resistances of the transmitter (TX) and receiver (RX) coils respectively. The circuit has two diodes $D_{anode}$ and $D_{cathode}$ that help in selective RF rectification. The components $L_{afb}$, $L_{cfb}$, $C_{afb}$ and $C_{cfb}$ are the frequency selecting components. The subscript "afb" stands for anodic frequency block and "cfb" stands for cathodic frequency block. These components help control the conduction/attenuation of the RF frequencies during anodic and cathodic phases. $V_s$ refers to source voltage, $R_{LOAD}$ and $C_{LOAK}$ refer to load resistance and capacitance respectively. Current flowing through the load resistor is given by $I(R_{LOAD})$.

Figure 28A:
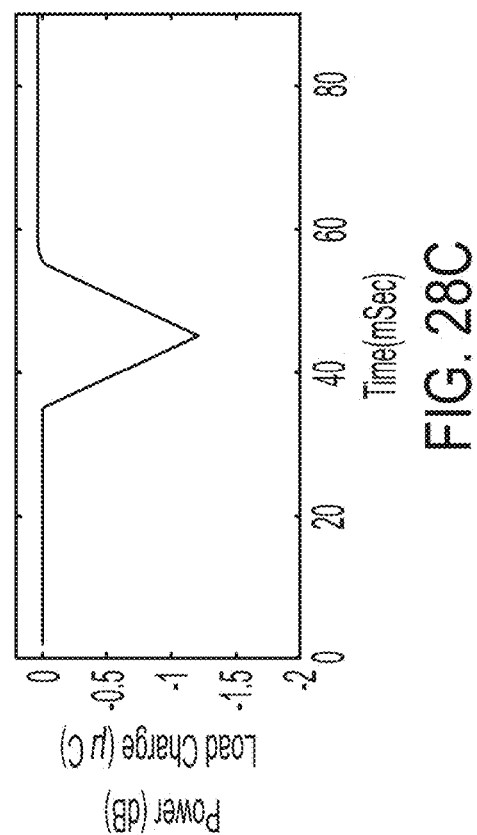
FIG. 28A illustrates a frequency graph according to an aspect of the present disclosure.
Figure 28B:
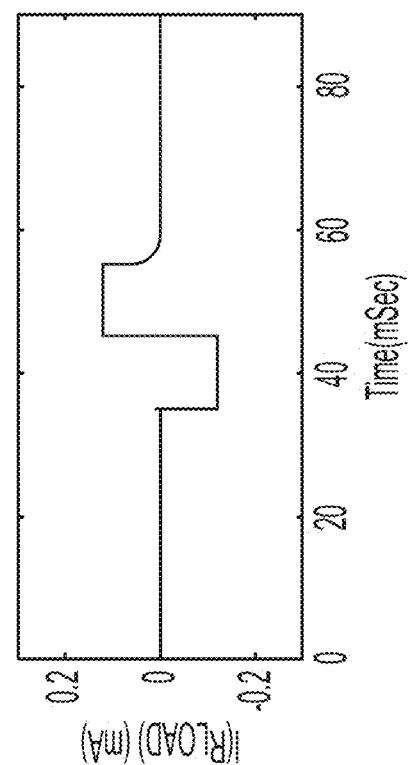
FIG. 28B illustrates an input voltage waveform graph according to an aspect of the present disclosure.

The circuit 202 diagram and the parameter values shown in FIG. 27 is simulated using the input voltage waveform shown in FIGS. 28A-28B. FIG. 28A illustrates a frequency graph and FIG. 28B illustrates an input voltage waveform graph. Time frequency analysis of the input voltage signal is plotted in FIG. 28A. The input waveform has two different RF carrier frequencies for anodic and cathodic phases as plotted in the time-frequency analysis graph. The use of two different RF carrier frequencies allows for the delivery of symmetric, square stimulation pulse to the load when used with the circuit shown in FIG. 27. In the designed input waveform, cathodic pulse has a cathodic RF frequency ($f_{C-RF}$) of about 500 kHz and anodic RF frequency ($f_{A-RF}$) of about 1000 kHz. The choice of anodic and cathodic RF carrier frequency is determined by the ability of the frequency selection offered by the receiver components such as $L_{afb}$, $C_{afb}$, $L_{cfb}$ and $C_{cfb}$.

Figure 28C:
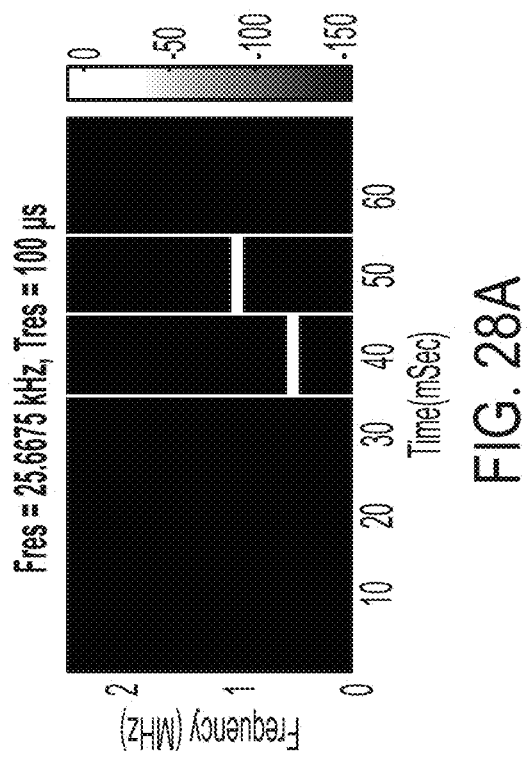
FIG. 28C illustrates a load charge delivered to a load resistor of the circuit of FIG. 27 according to an aspect of the present disclosure.
Figure 28D:
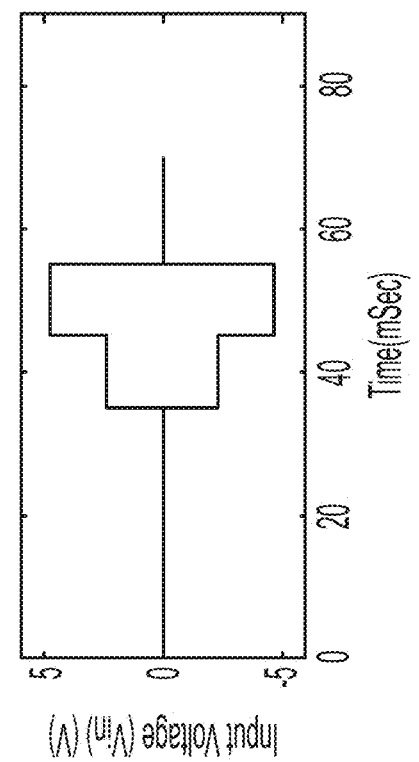
FIG. 28D illustrates the load current of the circuit in FIG. 27 according to an aspect of the present disclosure.
Figure 29A:
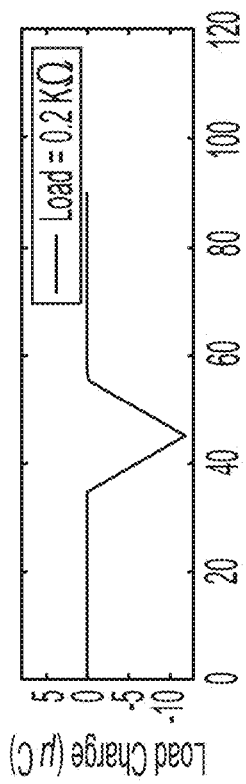
FIG. 29A illustrates a load current waveform according to an aspect of the present disclosure.
Figure 29B:
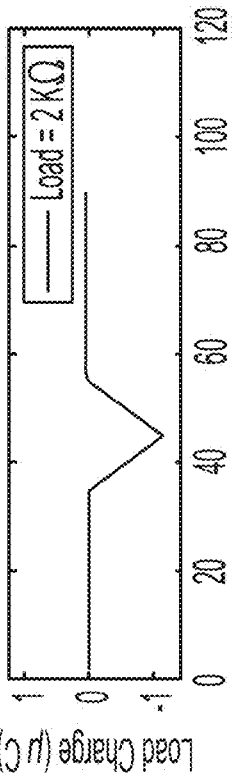
FIG. 29B illustrates a load current waveform according to an aspect of the present disclosure.
Figure 29C:
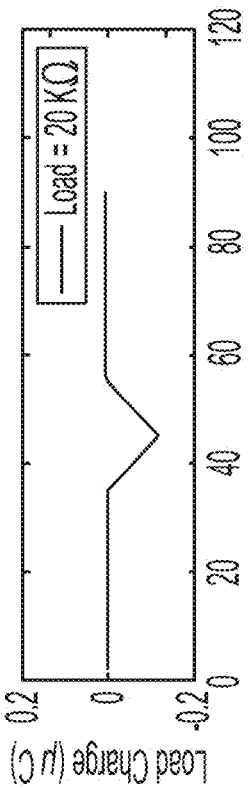
FIG. 29C illustrates a load current waveform according to an aspect of the present disclosure.
Figure 29D:
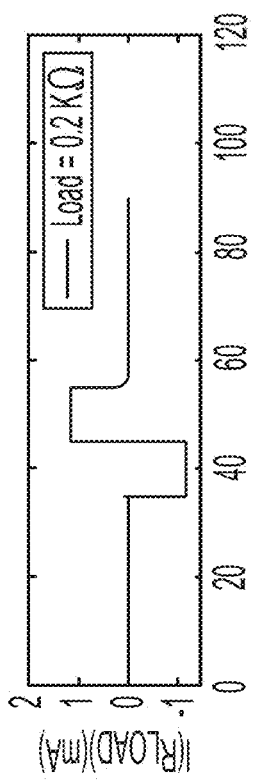
FIG. 29D illustrates a load charge delivery according to an aspect of the present disclosure.
Figure 29E:
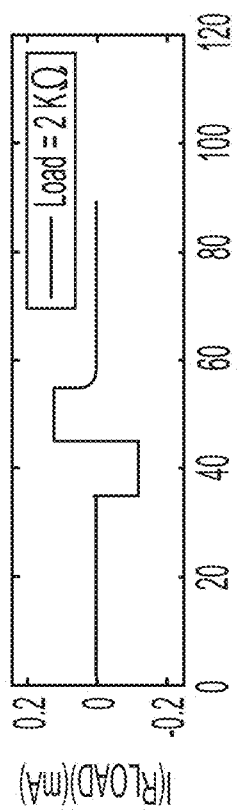
FIG. 29E illustrates a load charge delivery according to an aspect of the present disclosure.
Figure 29F:
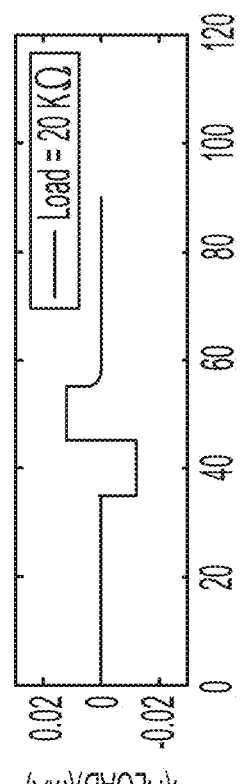
FIG. 29F illustrates a load charge delivery according to an aspect of the present disclosure.

The resulting load current $I(R_{LOAD})$ and the charge delivered to the load in the circuit 202 diagram of FIG. 27 is shown in FIGS. 28C-28D. FIG. 28C illustrates a load charge delivered to a load resistor of the circuit of FIG. 27 and FIG. 28D illustrates the load current of the circuit 202 in FIG. 27. It may be observed that the shape of the current waveform is very close to symmetric square wave. Also, the circuit 202 ensures that the current delivered to the load is charge balanced.

Induced voltage in the receiver coil conducts current through $D_{cathode}$ during cathodic phase and $D_{anode}$ during the anodic phase. The use of $L_{cfb}$ and $C_{cfb}$ helps reduce or block the cathodic RF frequency conduction but offers low impedance path to the anodic conduction. The use of $L_{afb}$ and $C_{afb}$ helps reduce or block the anodic RF frequency conduction but offers low impedance path to the cathodic conduction. Frequency dependency of the impedances offered by the parallel LC components implies that there is a leakage of the anodic current in the cathodic path and vice versa.

The circuit 202 design must be made independent of the load capacitor $C_{LOAD}$. The negative charging of the load capacitor must be quickly discharged to zero voltage before the onset of the anodic phase and then charge to positive voltage. Another constraint is that the peak current value in the anodic and cathodic phases delivered to the load ($I(R_{LOAD})$) must be comparable/same to achieve symmetry. Yet another constraint is that the charge balance must be obtained at all the load resistor values so that the stimulation safety may be assured. These constraints or the design goals may be obtained by appropriately choosing the anodic and cathodic RF frequencies ($f_{C-RF}$ and $f_{A-RF}$) at the transmitter side. Also, tuning the values of the $L_{afb}$, $C_{afb}$, $L_{cfb}$ and $C_{cfb}$ controls the conduction and leakage of the RF currents that determine the amplitude and charging times of the load current. Once these values are tuned, it is observed from a SPICE simulation that the shape of the load current waveform ($I(R_{LOAD})$) and the charge balance property remain independent of the load resistor value as shown in FIGS. 29A-29F.

A two-electrode system may provide more control over the stimulation region and performance. FIG. 30A illustrates a contact lens E-lens system 204 on the retina with a single stimulation electrode. The two circular metallic electrode plates 206 enable current conduction by providing forward and reverse path to the flow. The single electrode system may be controlled using the circuit 202 shown in FIG. 27.

Figure 31:
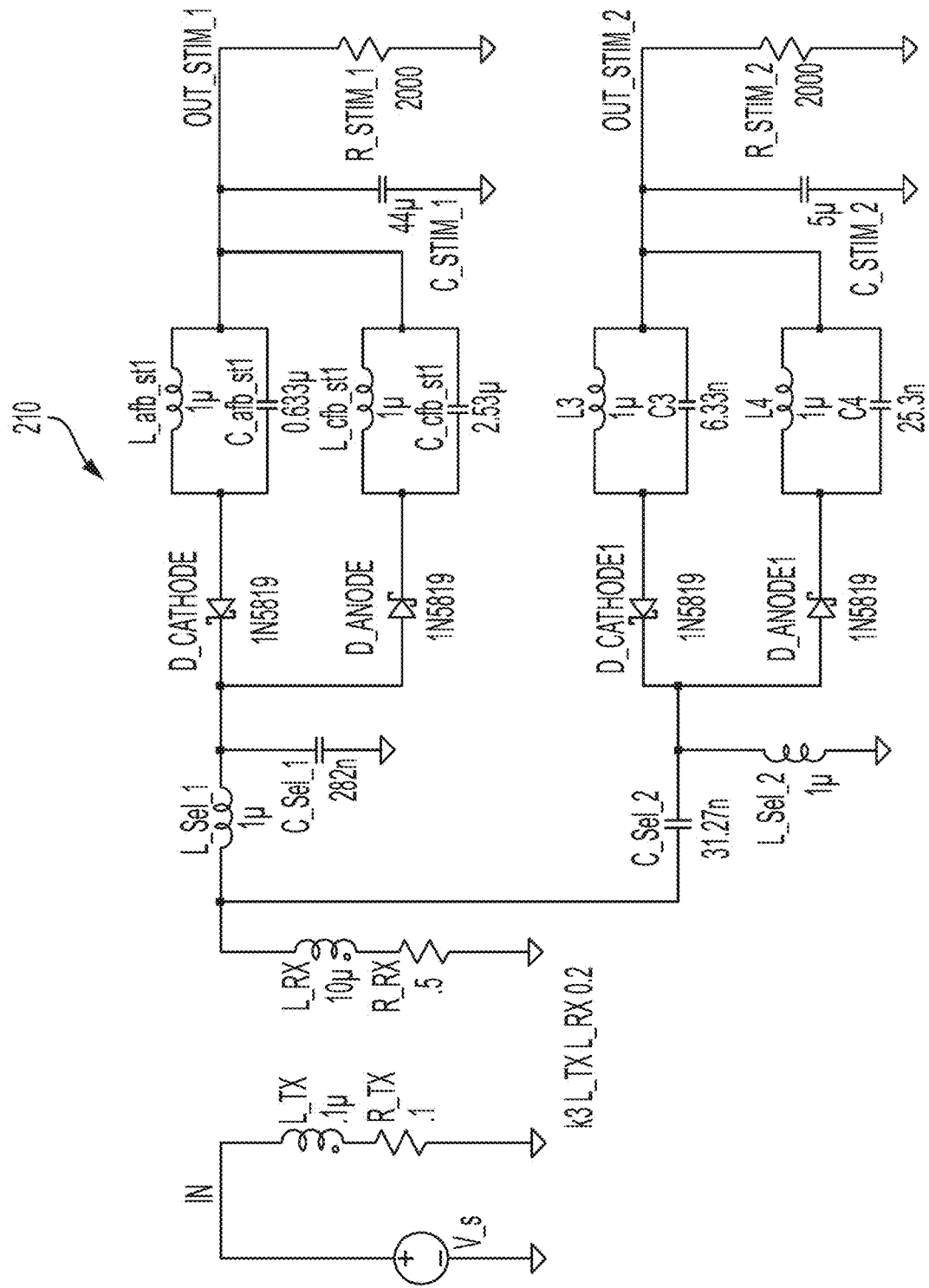
FIG. 31 illustrates a circuit schematic of a system that may provide wireless stimulation waveform to two stimulating electrodes independently according to an aspect of the present disclosure.

FIG. 30B illustrates a contact lens E-lens system 208 on the retina with two stimulation electrodes. The two-stimulation-electrode system may be controlled using a circuit 210 shown in FIG. 31. The circuit of FIG. 31 has two load resistors $R_{STIM-1}$ and $R_{STIM-2}$ indicating the load offered by the two stimulating electrodes. The current flowing in these two stimulation loads is given by $I(R_{STIM-1})$ and $I(R_{STIM-2})$ respectively. The RF path separation between the two electrodes is obtained by the choice of $L_{SEL-1}$, $C_{SEL-1}$, $L_{SEL-2}$ and $C_{SEL-2}$ values.

The input voltage waveforms necessary to independently control the stimulation of the two electrodes wirelessly from the transmitter side is shown in FIGS. 32A-32B. The time frequency analysis of the input waveform is shown in FIG. 32A. FIG. 32B illustrates an input voltage waveform to independently control the two electrodes wirelessly. The time frequency analysis plot helps differentiate between the four carrier frequencies that may independently control the stimulation of two electrodes and deliver symmetric anodic and cathodic waveforms for each electrode. The circuit 210 shown in FIG. 31 when simulated with the described input voltage provides the stimulating current $I(R_{STIM-1})$ and $I(R_{STIM-2})$ to the two stimulators shown in FIGS. 32C-32D. FIG. 32C illustrates a load current flowing in a load of the circuit of FIG. 31. FIG. 32D illustrates a load current flowing in a load of the circuit 210 of FIG. 31. The two electrodes operate at four different carrier frequencies and may provide a symmetric biphasic current waveform.

Figure 33:
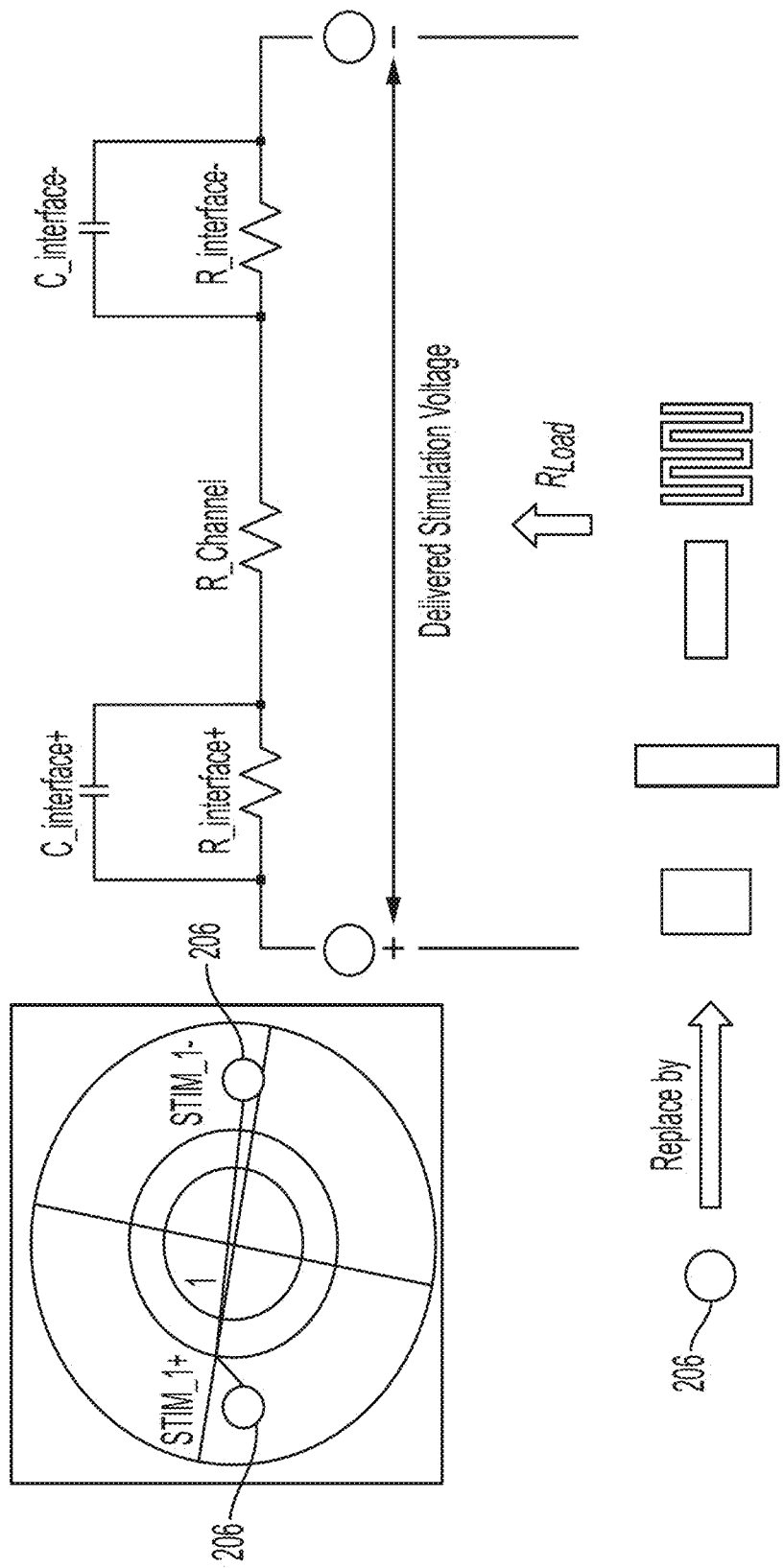
FIG. 33 illustrates constraints on an electrode design and available degrees of freedom according to an aspect of the present disclosure.

The impedance looking into the electrodes of an implanted E-lens may be capacitive due to presence of the interface capacitance. The circuit 210 (see FIG. 31) delivers a square wave to the resistive load. To maintain the same shape of the delivered current, it needs to be ensured that the stimulation system load is resistive. Hence, design must optimize the electrode-electrolyte impedance to be smaller than the channel resistance. To achieve this, the electrodes 206 are placed diagonally opposite on the E-lens system as shown in FIG. 33. FIG. 33 illustrates constraints on an electrode design and available degrees of freedom. Also, the circular electrodes 206 may each be replaced by square, rectangular, or serpentine electrodes to achieve the desired electrode-electrolyte impedance.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A system for providing electrical stimulation, comprising:
   a circuit configured to generate and wirelessly transmit a charge balanced and load independent stimulation waveform;
   a battery-less passive receiver coil configured to wirelessly receive the stimulation waveform;
   a first stimulating electrode electrically connected to the battery-less passive receiver coil and configured to be placed on a first portion of an eye of a patient and to receive the stimulation waveform;
   a return electrode electrically connected to the battery-less passive receiver coil and configured to be placed on a second portion of the eye such that current or voltage distribution is focalized to the eye and induced electric fields to an area of interest on or into the eye are maximized, wherein the electric fields provide neuroprotection and reinnervation;
   a ground electrically connected to the first stimulating electrode or the return electrode, the ground configured to be placed on a head of the patient, on skin adjacent to the eye or a non-stimulated eye or on a temporal area of the eye or the non-stimulated eye to induce the electric fields; and
   a passive electrode not electrically connected to the battery-less passive receiver coil and configured to be placed on the head of the patient to induce the electric fields in a brain and/or an optic nerve of the patient.

2. The system of claim 1, wherein the stimulation waveform is of long pulse durations to stimulate the eye and induce the electric fields to create epigenetic changes.

3. The system of claim 1, wherein responses of retinal neurons to transcorneal electrical stimulation of various stimulus parameters are analyzed.

4. The system of claim 1, wherein the area of interest on the eye includes a retina and an optic nerve, a ciliary body, a lacrimal gland, or a cornea including corneal nerves.

5. The system of claim 1, further comprising:
   a second stimulating electrode electrically connected to the battery-less passive receiver coil,
   wherein the circuit is further configured to independently control stimulation of the first stimulating electrode and the second stimulating electrode from a transmitter end.

6. The system of claim 1, further comprising a power source configured to supply power to the system.

7. The system of claim 6, wherein the power source is a battery configured to be placed on the eye, a temporal site of the eye, eyeglasses, a head of the patient, or behind an ear of the patient.

8. A system for providing electrical stimulation, comprising:
   a circuit configured to generate or receive a stimulation waveform;
   a stimulating electrode electrically connected to the circuit and configured to be placed on a first portion of an eye of a patient;
   a return electrode electrically connected to the circuit and configured to be placed on a second portion of the eye, the second portion being posterior to the first portion, such that voltage distribution is focalized to a central nervous system (CNS) and induced electric fields to an area of interest are maximized; and
   a passive electrode not electrically connected to the circuit and configured to be placed on a forehead or a back of a head of the patient to induce the electric fields in layers of the CNS,
   wherein the electric fields provide neuroprotection and reinnervation.

9. The system of claim 8, wherein a symmetric biphasic charge-balanced waveform of long pulse durations is used to stimulate the eye and induce the electric fields to create epigenetic changes in the CNS.

10. The system of claim 8, wherein the area of interest includes later geniculate, visual cortex, superior colliculus, motor cortex, frontal cortex, sensory cortex, other visual cortical areas, hippocampus, other subcortical regions, brainstem, or areas associated with the brainstem.

11. A system for providing electrical stimulation, comprising:
   a circuit configured to generate and wirelessly transmit a symmetric biphasic charge-balanced waveform;
   a battery-less passive receiver coil configured to wirelessly receive the symmetric biphasic charge-balanced waveform;
   a stimulating electrode electrically connected to the battery-less passive receiver coil and configured to be placed on a first portion of an eye of a patient;

a return electrode electrically connected to the battery-less passive receiver coil and configured to be placed on a second portion of the eye such that a current density distribution is maximized along an optic nerve and in a superior colliculus; and a passive electrode not electrically connected to the battery-less passive receiver coil and configured to be placed on a head of the patient to induce the electric fields in a brain and/or the optic nerve of the patient.

12. The system of claim 1, wherein the first portion is adjacent to the second portion.

13. The system of claim 1, further comprising one or more resonating capacitors electrically connected to the battery-less passive receiver coil.

14. The system of claim 8, wherein the circuit includes a battery-less passive receiver coil electrically connected to the stimulating electrode and configured to wirelessly receive a symmetric biphasic charge-balanced waveform.

15. The system of claim 14, further comprising one or more resonating capacitors electrically connected to the battery-less passive receiver coil.

16. The system of claim 11, further comprising a contact lens configured to be placed on the eye and to house the battery-less passive receiver coil.

17. The system of claim 16, further comprising one or more resonating capacitors electrically connected to the battery-less passive receiver coil.

18. The system of claim 1, wherein the passive electrode is not electrically connected to the stimulating electrode and is not electrically connected to the return electrode.

* * * * *

UNITED STATES PATENT AND TRADEMARK OFFICE
CERTIFICATE OF CORRECTION

| | | |
|---|---|---|
| PATENT NO. | : 12,427,303 B2 | Page 1 of 1 |
| APPLICATION NO. | : 17/685186 | |
| DATED | : September 30, 2025 | |
| INVENTOR(S) | : Mark S. Humayun et al. | |

It is certified that error appears in the above-identified patent and that said Letters Patent is hereby corrected as shown below:

In the Specification

Column 1, Lines 21-26, under "STATEMENT AS TO FEDERALLY SPONSORED RESEARCH" heading, delete the entire paragraph and replace with the following:

This invention was made with government support under grant number 1933394 awarded by the National Science Foundation. The government has certain rights in the invention.

Signed and Sealed this
Fourth Day of November, 2025

John A. Squires
*Director of the United States Patent and Trademark Office*